US006960221B2

(12) United States Patent
Ho et al.

(10) Patent No.: US 6,960,221 B2
(45) Date of Patent: Nov. 1, 2005

(54) TISSUE CONNECTOR APPARATUS WITH CABLE RELEASE

(75) Inventors: Liem Ho, Mountain View, CA (US); Isidro Matias Gandionco, Fremont, CA (US); Nga T. Doan, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 74 days.

(21) Appl. No.: 10/188,013

(22) Filed: Jul. 1, 2002

(65) Prior Publication Data

US 2003/0093118 A1 May 15, 2003

Related U.S. Application Data

(63) Continuation of application No. 09/259,705, filed on Mar. 1, 1999, now Pat. No. 6,514,265.

(51) Int. Cl.[7] .............................................. A61B 17/08
(52) U.S. Cl. .................................................. 606/157
(58) Field of Search ................................ 606/157, 151, 606/200, 217, 213, 216, 218, 221, 225, 227, 606/232, 233; 403/300, 291, 326, 327

(56) References Cited

U.S. PATENT DOCUMENTS

| 43,098 A | 6/1864 | Cooper |
| 655,190 A | 8/1900 | Bramson |
| 1,583,271 A | 5/1926 | Biro |
| 1,625,602 A | 4/1927 | Gould et al. |
| 2,240,330 A | 4/1941 | Flagg et al. |
| 2,256,382 A | 9/1941 | Dole |
| 2,264,679 A | 12/1941 | Ravel |
| 2,516,710 A | 7/1950 | Mascolo |
| 2,715,486 A | 8/1955 | Marcoff-Moghadam et al. |
| 2,890,519 A | 6/1959 | Storz, Jr. |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,875,648 A | 4/1975 | Bone |
| 3,910,281 A | 10/1975 | Kletschka et al. |
| 3,958,576 A | 5/1976 | Komiya |
| 4,038,725 A | 8/1977 | Keefe |
| 4,140,125 A | 2/1979 | Smith |
| 4,170,990 A | 10/1979 | Baumgart et al. |
| 4,192,315 A | 3/1980 | Hilzinger et al. |

(Continued)

FOREIGN PATENT DOCUMENTS

DE  21 99 99  3/1910

(Continued)

OTHER PUBLICATIONS

Written Opinion PCT/US99/12563 (Jun. 12, 2000).

(Continued)

Primary Examiner—(Jackie) Tan-Uyen T. Ho
(74) Attorney, Agent, or Firm—Tom Berry; Jeff Hohenshell

(57) ABSTRACT

A tissue connector assembly comprising a clip movable between an open configuration and a closed configuration and a mechanical restraining device including a plurality of strands releasably attachable to the clip for restraining the clip in its open configuration. A needle may be releasably attached to the clip. A flexible member may also interconnect the clip and the needle.

37 Claims, 16 Drawing Sheets

U.S. PATENT DOCUMENTS

| | | | |
|---|---|---|---|
| 4,217,902 | A | 8/1980 | March |
| 4,324,248 | A | 4/1982 | Perlin |
| 4,345,601 | A | 8/1982 | Fukuda |
| 4,416,266 | A | 11/1983 | Baucom |
| 4,456,017 | A | 6/1984 | Miles |
| 4,485,816 | A | 12/1984 | Krumme |
| 4,522,207 | A | 6/1985 | Klieman et al. |
| 4,535,764 | A | 8/1985 | Ebert |
| 4,549,545 | A | 10/1985 | Levy |
| 4,586,502 | A | 5/1986 | Bedi et al. |
| 4,586,503 | A | 5/1986 | Kirsch et al. |
| 4,595,007 | A | 6/1986 | Mericle |
| 4,612,932 | A | 9/1986 | Caspar et al. |
| 4,637,380 | A | 1/1987 | Orejola |
| 4,665,906 | A | 5/1987 | Jervis |
| 4,683,895 | A | 8/1987 | Pohndorf |
| 4,719,924 | A | 1/1988 | Crittenden et al. |
| 4,730,615 | A | 3/1988 | Sutherland et al. |
| 4,809,695 | A | 3/1989 | Gwathmey et al. |
| 4,873,975 | A | 10/1989 | Walsh et al. |
| 4,896,668 | A | 1/1990 | Popoff et al. |
| 4,899,744 | A | 2/1990 | Fujitsuka et al. |
| 4,901,721 | A | 2/1990 | Hakki |
| 4,924,866 | A | 5/1990 | Yoon |
| 4,926,860 | A | 5/1990 | Stice et al. |
| 4,929,240 | A | 5/1990 | Kirsch et al. |
| 4,932,955 | A | 6/1990 | Merz et al. |
| 4,950,283 | A | 8/1990 | Dzubow et al. |
| 4,950,285 | A | 8/1990 | Wilk |
| 4,983,176 | A | 1/1991 | Cushman et al. |
| 4,997,439 | A | 3/1991 | Chen |
| 5,002,550 | A | 3/1991 | Li |
| 5,002,562 | A | 3/1991 | Oberlander |
| 5,002,563 | A | 3/1991 | Pyka et al. |
| 5,047,047 | A | 9/1991 | Yoon |
| 5,053,047 | A | 10/1991 | Yoon |
| 5,074,874 | A | 12/1991 | Yoon et al. |
| 5,123,913 | A | 6/1992 | Wilk et al. |
| 5,152,769 | A | 10/1992 | Baber |
| 5,154,189 | A | 10/1992 | Oberlander |
| 5,158,566 | A | 10/1992 | Pianetti |
| 5,171,252 | A | 12/1992 | Friedland |
| 5,174,087 | A | 12/1992 | Bruno |
| 5,196,022 | A | 3/1993 | Bilweis |
| 5,219,358 | A | 6/1993 | Bendel et al. |
| 5,222,976 | A | 6/1993 | Yoon |
| 5,236,440 | A | 8/1993 | Hlavacek |
| 5,242,456 | A | 9/1993 | Nash et al. |
| 5,246,443 | A | 9/1993 | Mai |
| 5,258,011 | A | 11/1993 | Drews |
| 5,269,783 | A | 12/1993 | Sander |
| 5,290,289 | A | 3/1994 | Sanders et al. |
| 5,304,204 | A | 4/1994 | Bregen |
| 5,312,436 | A | 5/1994 | Coffey et al. |
| 5,330,503 | A | 7/1994 | Yoon |
| 5,336,239 | A | 8/1994 | Gimpelson |
| 5,374,268 | A | 12/1994 | Sander |
| 5,383,904 | A | 1/1995 | Totakura et al. |
| 5,403,346 | A | 4/1995 | Loeser |
| 5,437,680 | A | 8/1995 | Yoon |
| 5,437,685 | A | 8/1995 | Blasnik |
| 5,439,479 | A | 8/1995 | Shichman et al. |
| 5,445,167 | A | 8/1995 | Yoon et al. |
| 5,452,733 | A | 9/1995 | Sterman et al. |
| 5,456,246 | A | 10/1995 | Schmieding et al. |
| 5,462,561 | A | 10/1995 | Voda |
| 5,474,557 | A | 12/1995 | Mai |
| 5,480,405 | A | 1/1996 | Yoon |
| 5,486,197 | A | 1/1996 | Le et al. |
| 5,500,000 | A | 3/1996 | Feagin et al. |
| 5,527,342 | A | 6/1996 | Pietrzak et al. |
| 5,533,236 | A * | 7/1996 | Tseng .................. 24/67.5 |
| 5,549,619 | A | 8/1996 | Peters et al. |
| 5,569,274 | A | 10/1996 | Rapacki et al. |
| 5,569,301 | A | 10/1996 | Granger et al. |
| 5,582,616 | A | 12/1996 | Bolduc et al. |
| 5,582,619 | A | 12/1996 | Ken |
| 5,586,983 | A | 12/1996 | Sanders et al. |
| 5,591,179 | A | 1/1997 | Edelstein |
| 5,593,414 | A | 1/1997 | Shipp et al. |
| 5,593,424 | A | 1/1997 | Northrup, III |
| 5,601,600 | A * | 2/1997 | Ton ..................... 606/206 |
| 5,609,608 | A | 3/1997 | Benett et al. |
| 5,632,752 | A | 5/1997 | Buelna |
| 5,632,753 | A | 5/1997 | Loeser |
| 5,643,295 | A | 7/1997 | Yoon |
| 5,645,568 | A | 7/1997 | Chervitz et al. |
| 5,665,109 | A | 9/1997 | Yoon |
| 5,683,417 | A | 11/1997 | Cooper |
| 5,695,505 | A | 12/1997 | Yoon |
| 5,697,943 | A | 12/1997 | Sauer et al. |
| 5,700,270 | A | 12/1997 | Peyser et al. |
| 5,700,271 | A | 12/1997 | Whitfield et al. |
| 5,707,380 | A | 1/1998 | Hinchliffe et al. |
| 5,709,693 | A | 1/1998 | Taylor |
| 5,709,695 | A | 1/1998 | Northrup, III |
| 5,725,539 | A | 3/1998 | Matern |
| 5,725,542 | A | 3/1998 | Yoon |
| 5,728,135 | A | 3/1998 | Bregen et al. |
| 5,735,290 | A | 4/1998 | Sterman et al. |
| 5,799,661 | A | 9/1998 | Boyd et al. |
| 5,810,851 | A | 9/1998 | Yoon |
| 5,849,019 | A | 12/1998 | Yoon |
| 5,879,371 | A | 3/1999 | Gardiner et al. |
| 5,891,160 | A | 4/1999 | Williamson, IV et al. |
| 5,941,434 | A | 8/1999 | Green |
| 5,961,481 | A | 10/1999 | Sterman et al. |
| 5,961,539 | A | 10/1999 | Northrup, III et al. |
| 5,972,024 | A | 10/1999 | Northrup, III et al. |
| 5,976,159 | A | 11/1999 | Bolduc et al. |
| 5,989,268 | A | 11/1999 | Pugsley, Jr. et al. |
| 5,997,556 | A | 12/1999 | Tanner |
| 6,013,084 | A | 1/2000 | Ken et al. |
| 6,139,540 | A | 10/2000 | Rost et al. |
| 6,176,413 | B1 | 1/2001 | Heck et al. |
| 6,193,734 | B1 | 2/2001 | Bolduc et al. |
| 6,254,615 | B1 | 7/2001 | Bolduc et al. |
| 6,296,622 | B1 * | 10/2001 | Kurz et al. .............. 604/93.01 |

FOREIGN PATENT DOCUMENTS

| | | |
|---|---|---|
| DE | 27 03 529 | 1/1977 |
| DE | 32 03 410 | 5/1981 |
| DE | 32 27 984 | 2/1984 |
| DE | 41 33 800 | 10/1991 |
| DE | 44 02 058 | 4/1995 |
| DE | 195 47 617 | 9/1997 |
| EP | 0 121 362 | 9/1987 |
| EP | 0 432 692 | 6/1991 |
| EP | 0 478 949 | 8/1991 |
| EP | 0 494 636 | 7/1992 |
| EP | 0 559 429 | 3/1993 |
| EP | 0 537 955 | 4/1993 |
| EP | 0 326 426 | 12/1994 |
| EP | 0 419 597 | 12/1994 |
| EP | 0 641 546 | 3/1995 |
| EP | 0 711 532 | 5/1996 |
| EP | 0 734 697 | 10/1996 |
| EP | 0 778 005 | 6/1997 |
| EP | 0 815 795 | 1/1998 |
| GB | 2 233 410 | 4/1990 |
| JP | 10337291 | 12/1998 |
| RU | 2110222 | 5/1998 |
| SU | 1186199 | 10/1985 |

| | | |
|---|---|---|
| SU | 1456109 | 2/1989 |
| SU | 1560133 | 4/1990 |
| WO | WO 90/06725 | 6/1990 |
| WO | WO 90/09149 | 8/1990 |
| WO | WO 90/14795 | 12/1990 |
| WO | WO 91/07916 | 6/1991 |
| WO | WO 91/17712 | 11/1991 |
| WO | WO 92/05828 | 4/1992 |
| WO | WO 94/15535 | 7/1994 |
| WO | WO 94/15537 | 7/1994 |
| WO | WO 96/00035 | 1/1996 |
| WO | WO 96/06565 | 3/1996 |
| WO | WO 96/38090 | 12/1996 |
| WO | WO 97/28744 | 8/1997 |
| WO | WO 97/32526 | 9/1997 |
| WO | WO 97/42881 | 11/1997 |
| WO | WO 98/30153 | 7/1998 |
| WO | WO 98/42262 | 10/1998 |

OTHER PUBLICATIONS

Emery et al. "Suture techniques for MIDCAB Surgery" Chapt 12, pp. 87-91.

"VCS Clip Applier System," published in 1995 by Auto Suture Company, a Division of U.S. Surgical Corporation (8 pages).

* cited by examiner

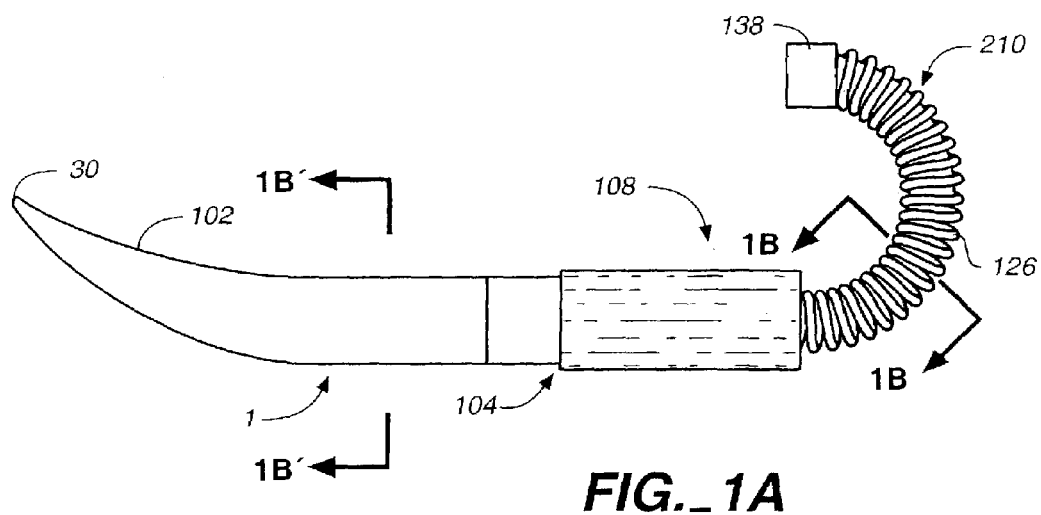
FIG._1A
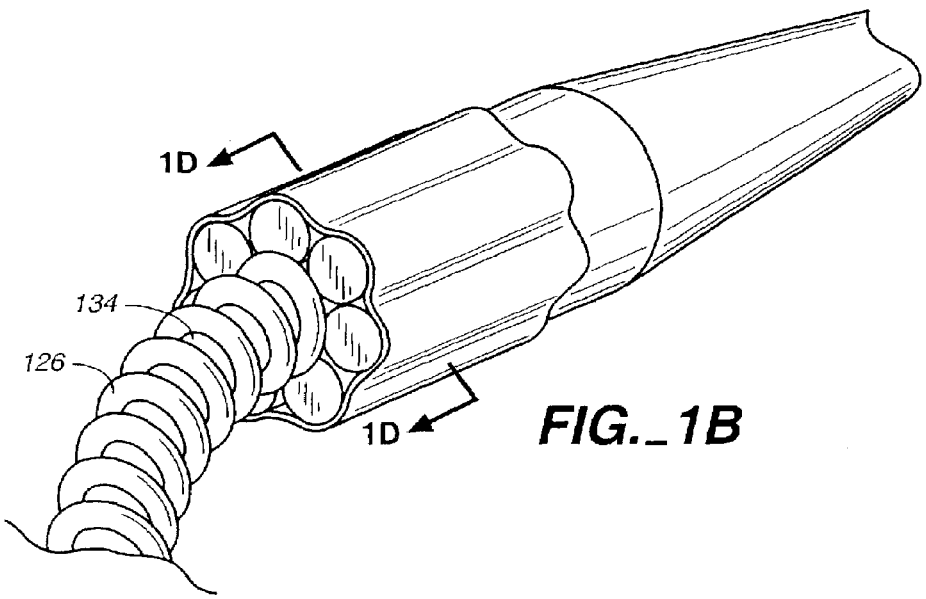
FIG._1B

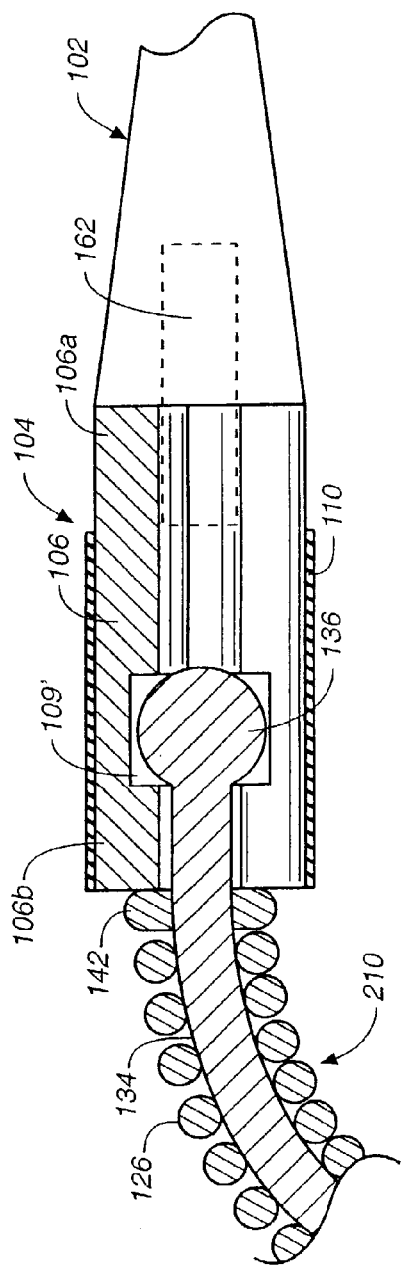
FIG._1C
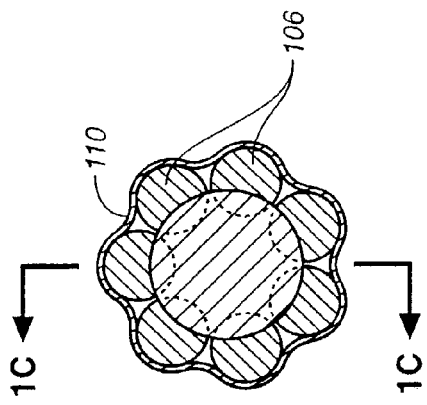
FIG._1D

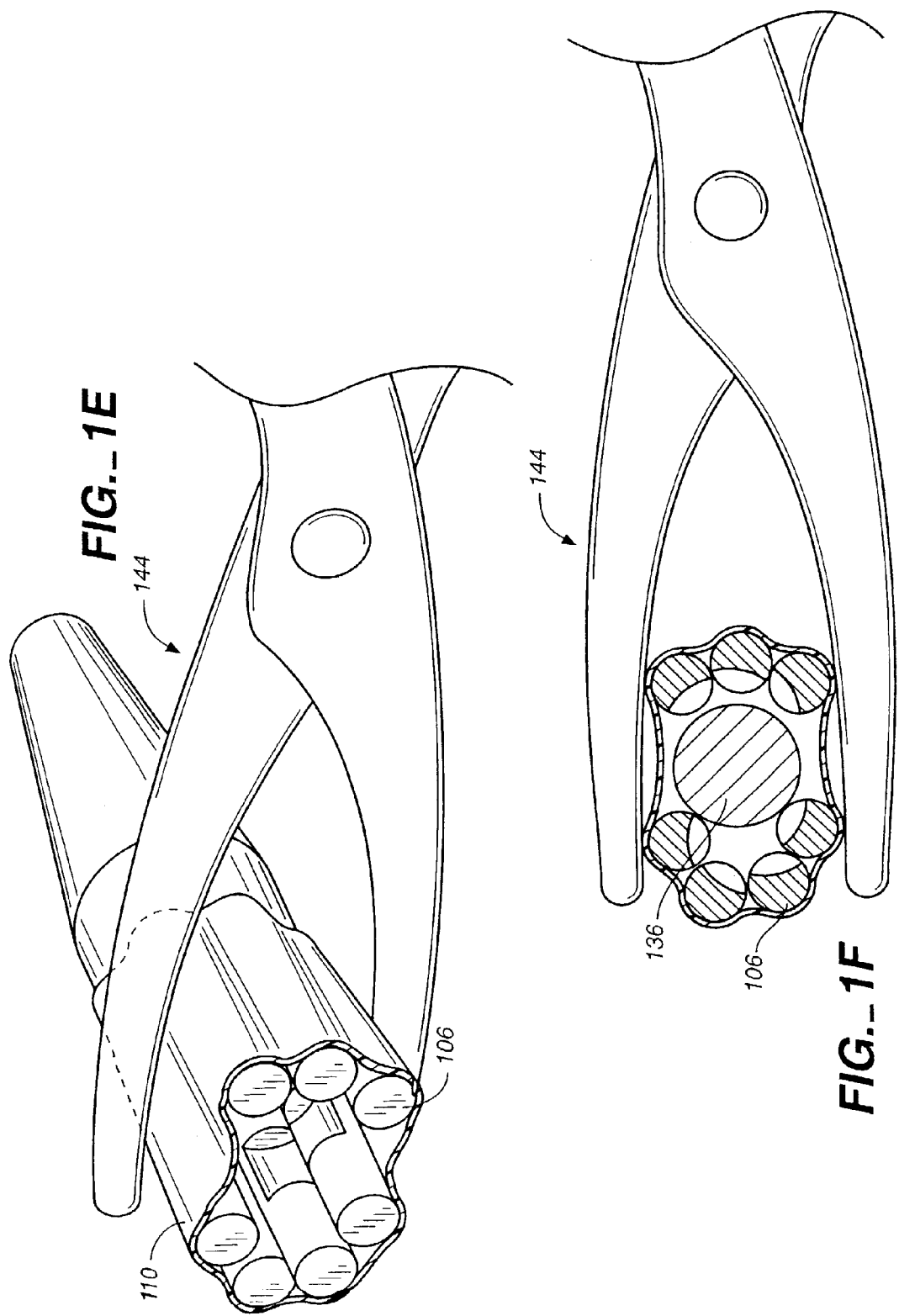

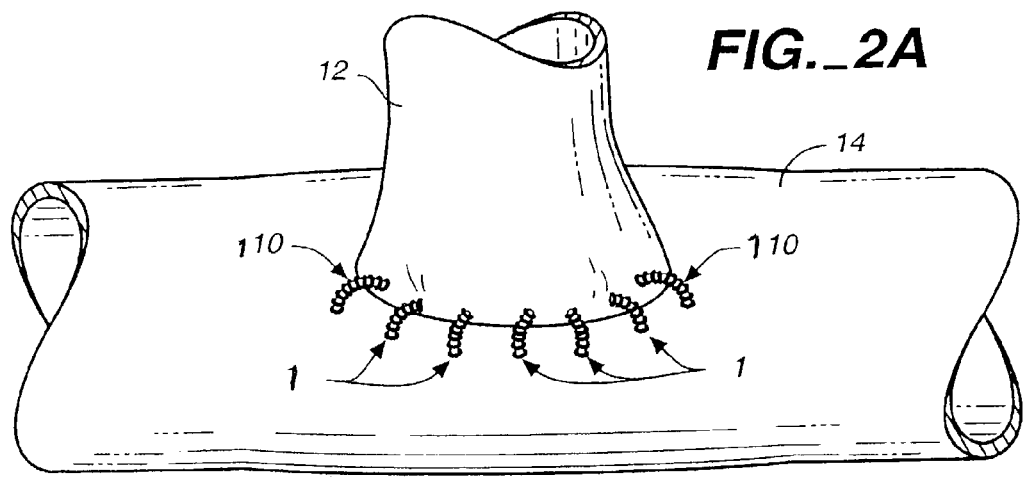
FIG._2A
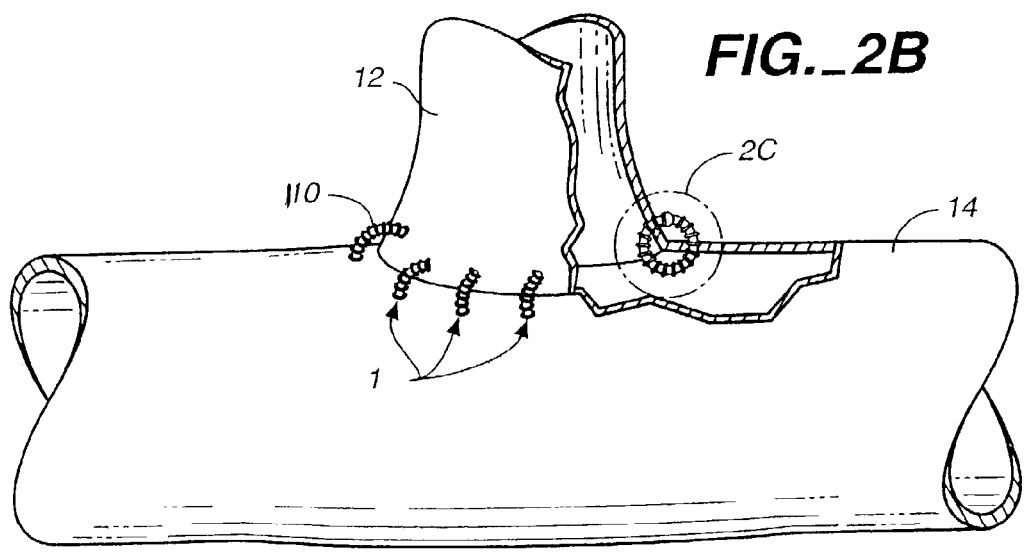
FIG._2B

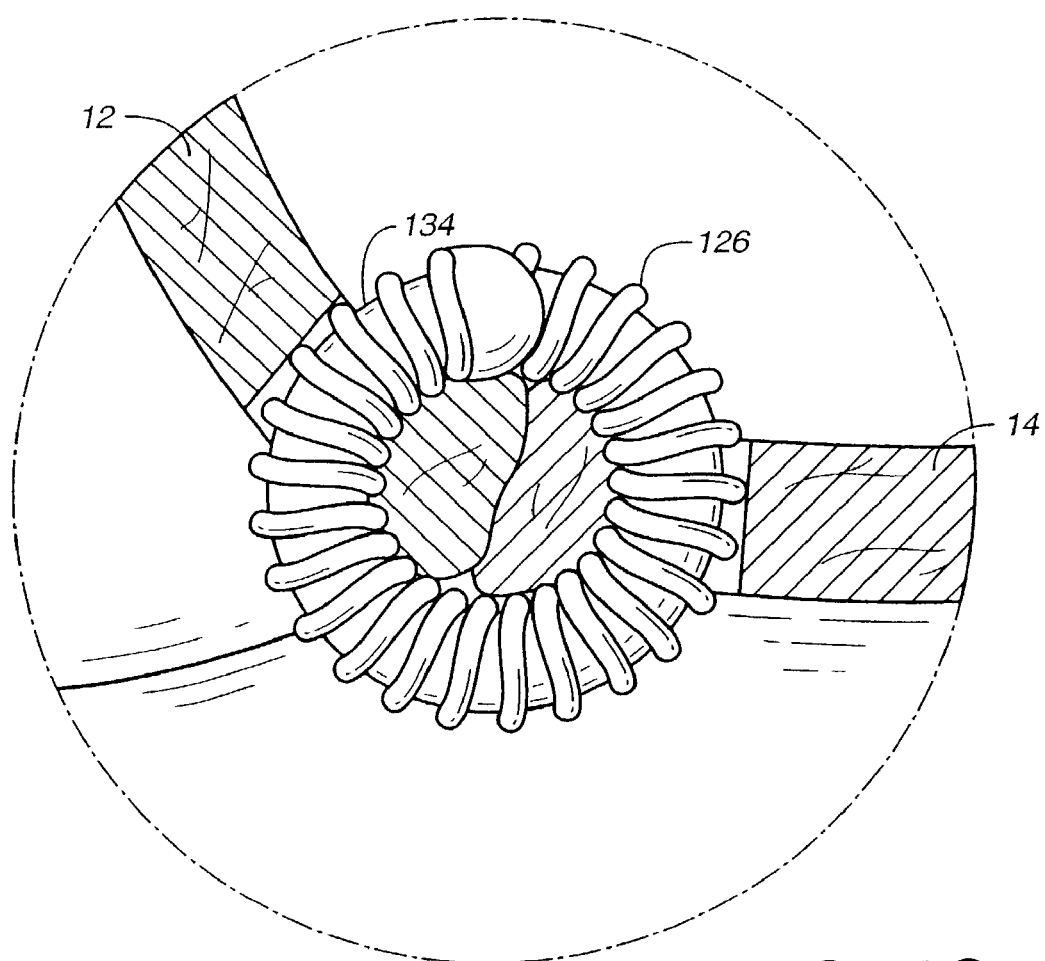
FIG._2C

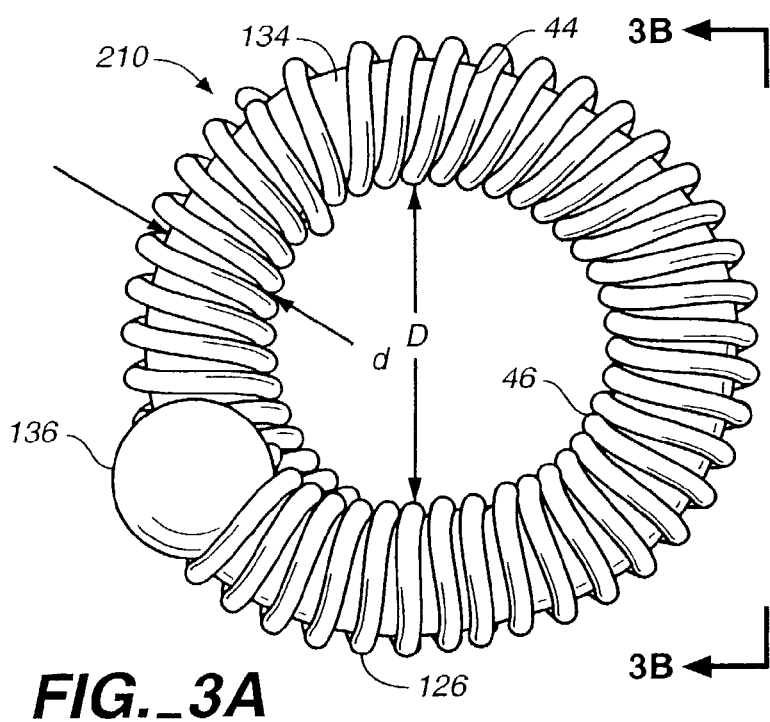
FIG._3A
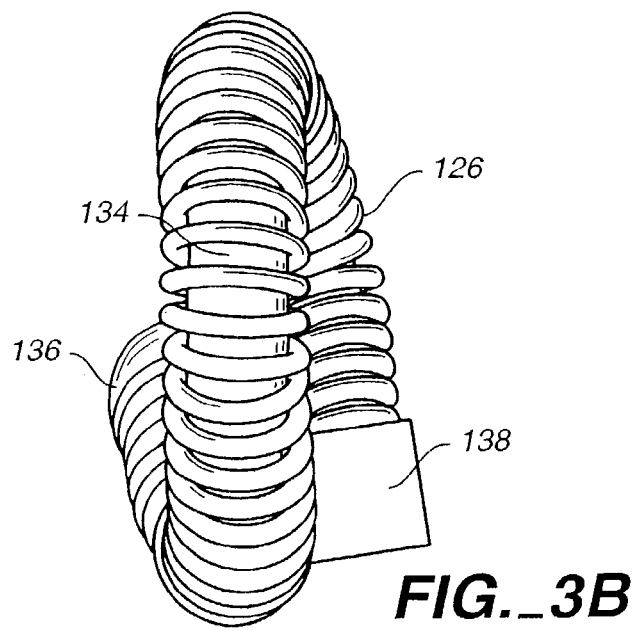
FIG._3B

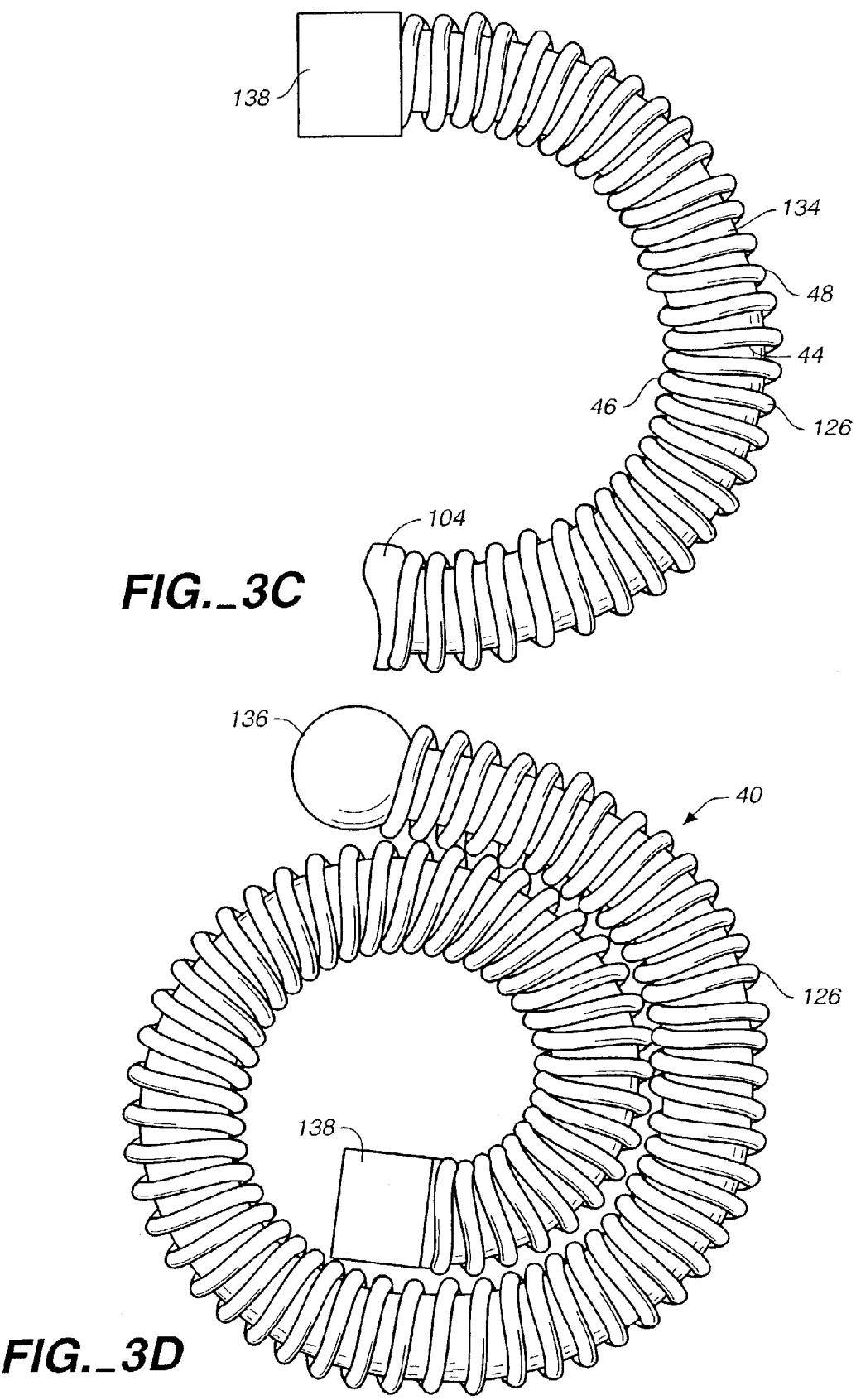

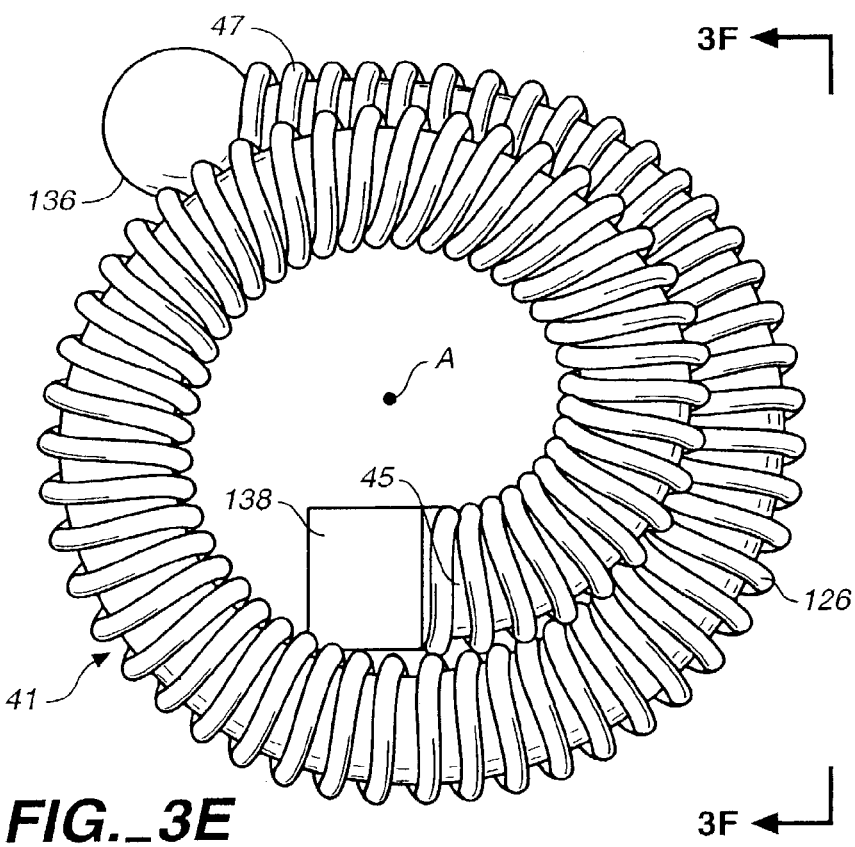
FIG._3E
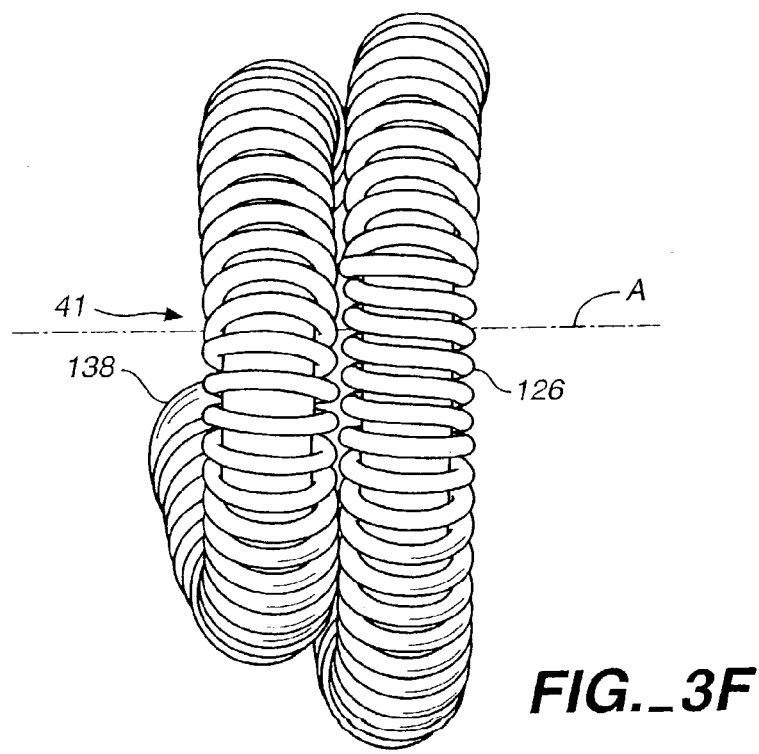
FIG._3F

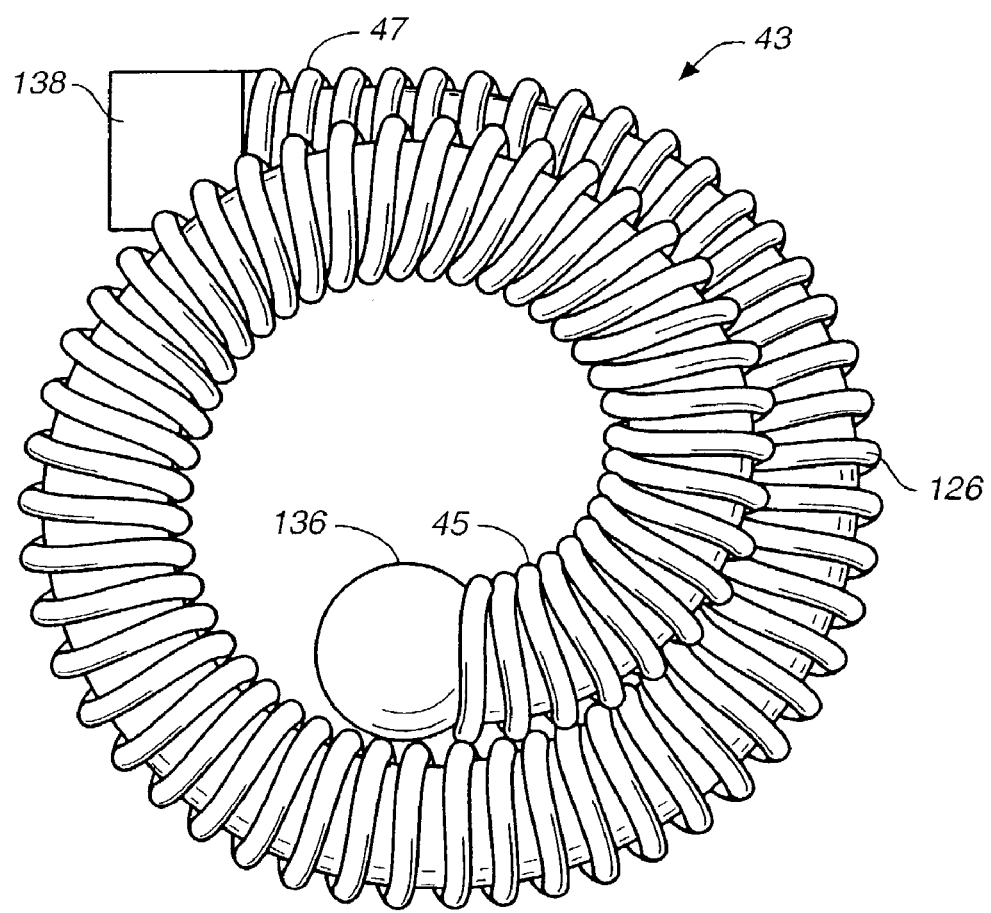
FIG._3G

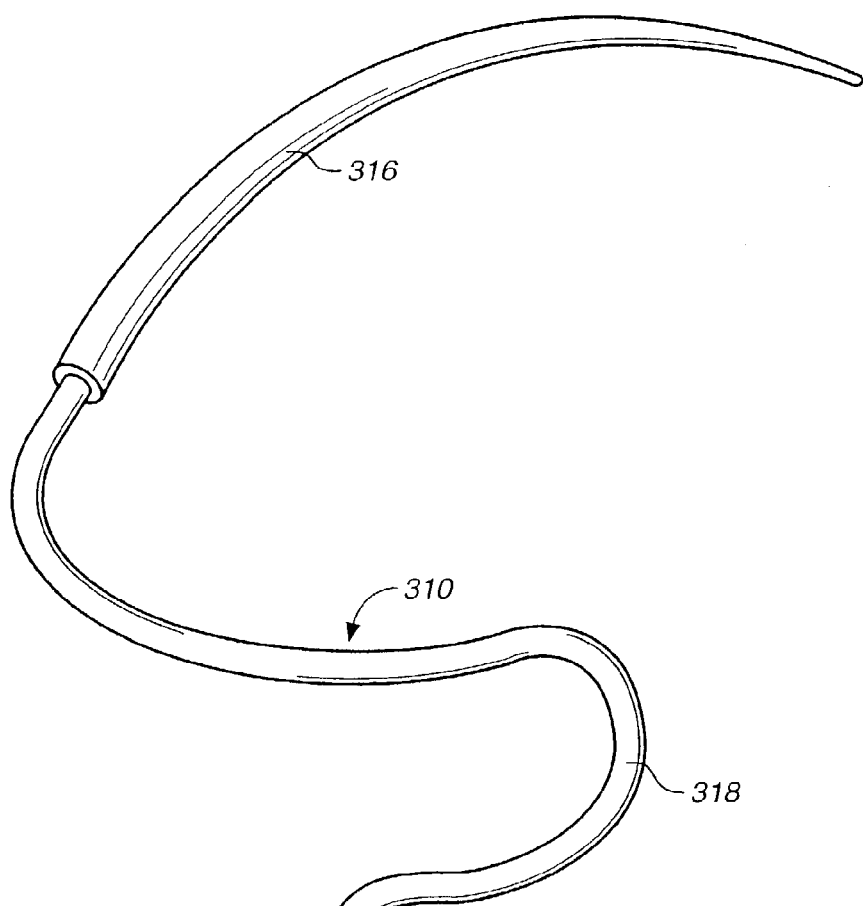
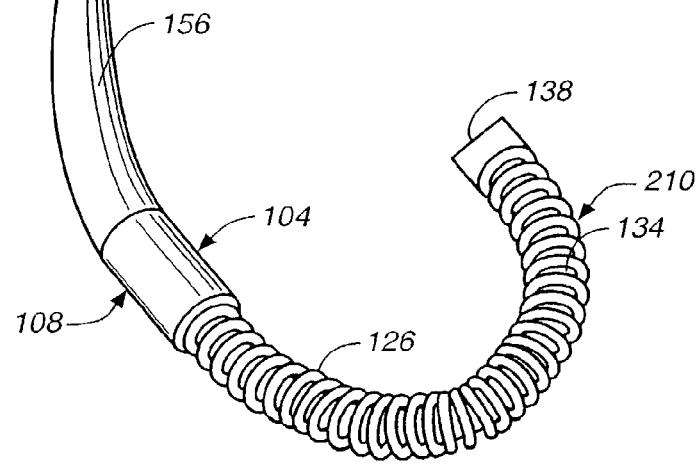
FIG._4

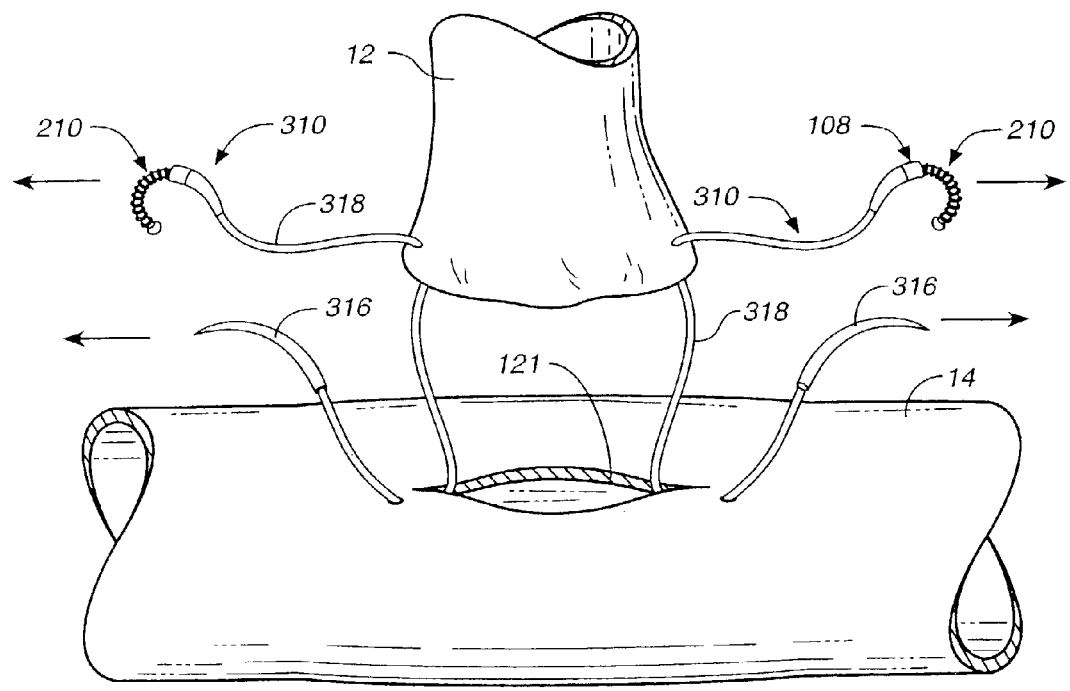
FIG._5
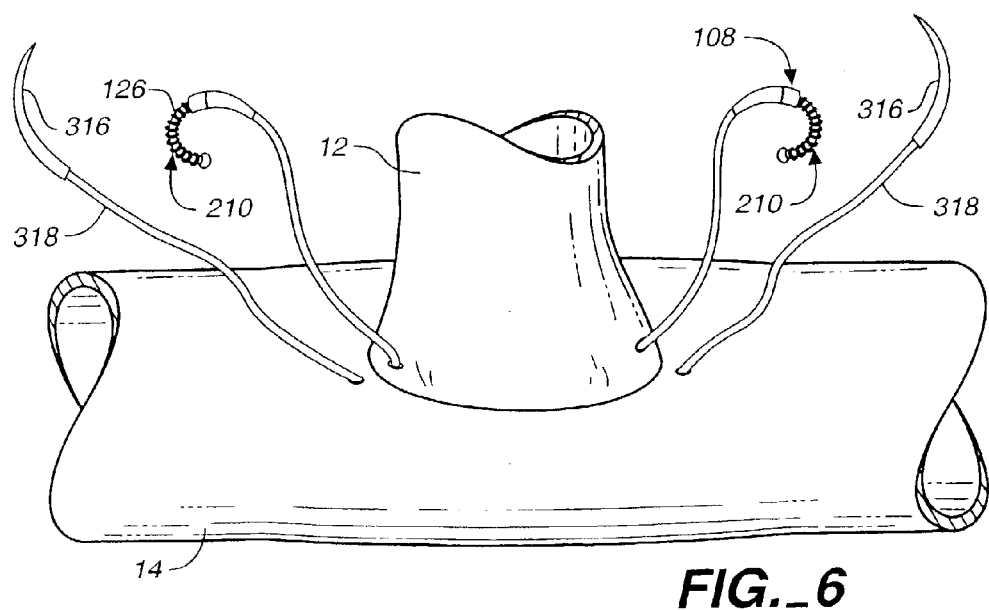
FIG._6

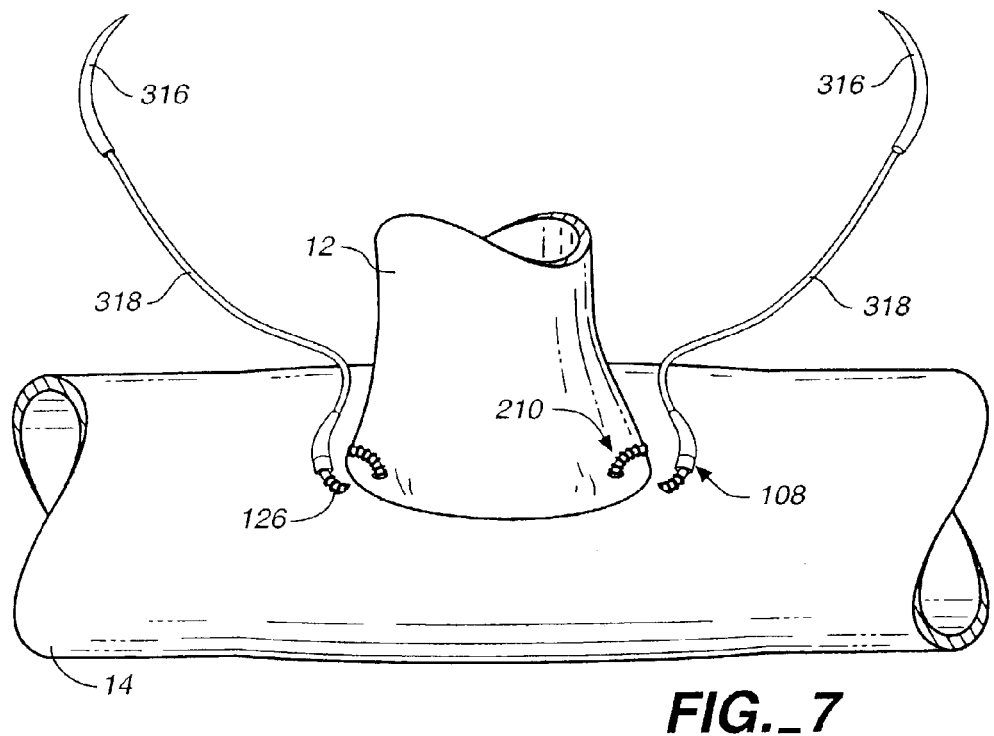
FIG._7
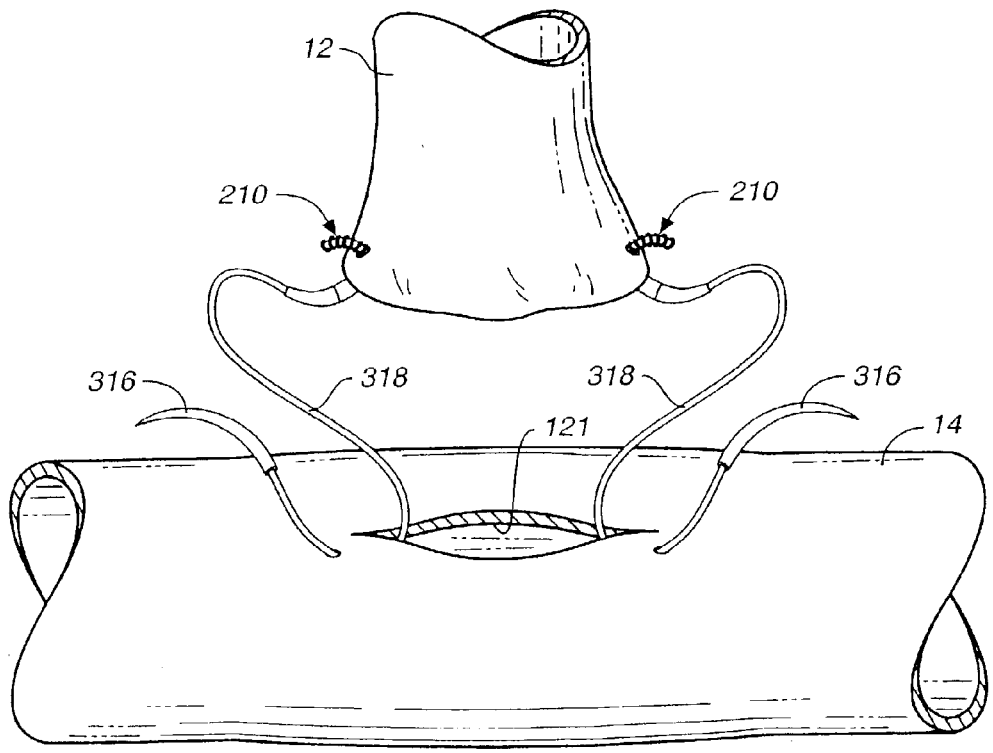
FIG._8

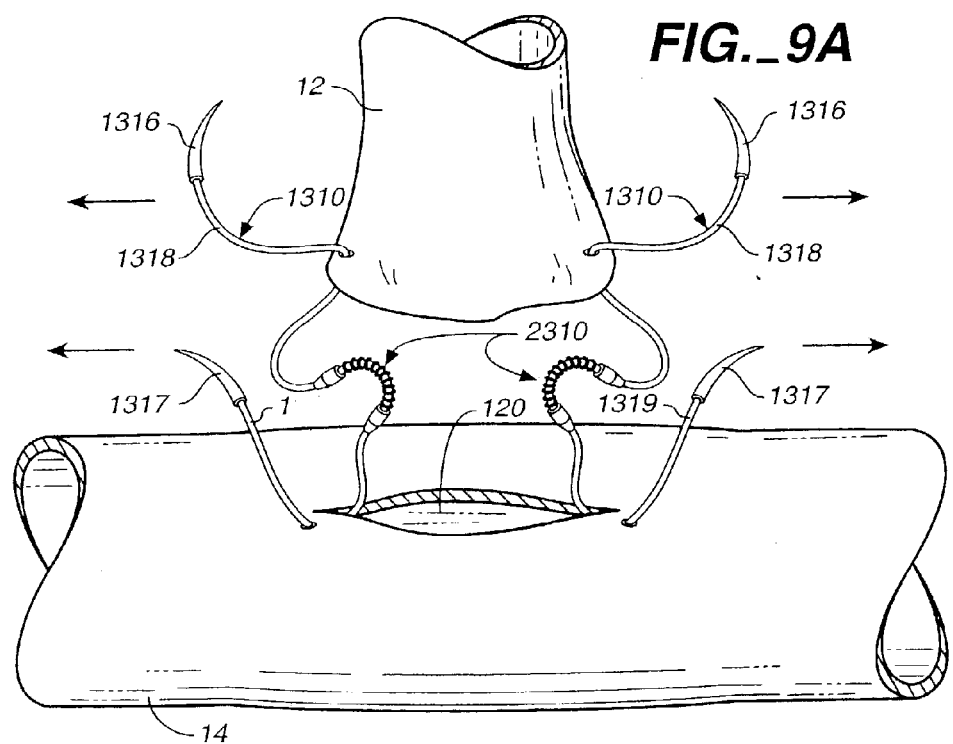
FIG._9A
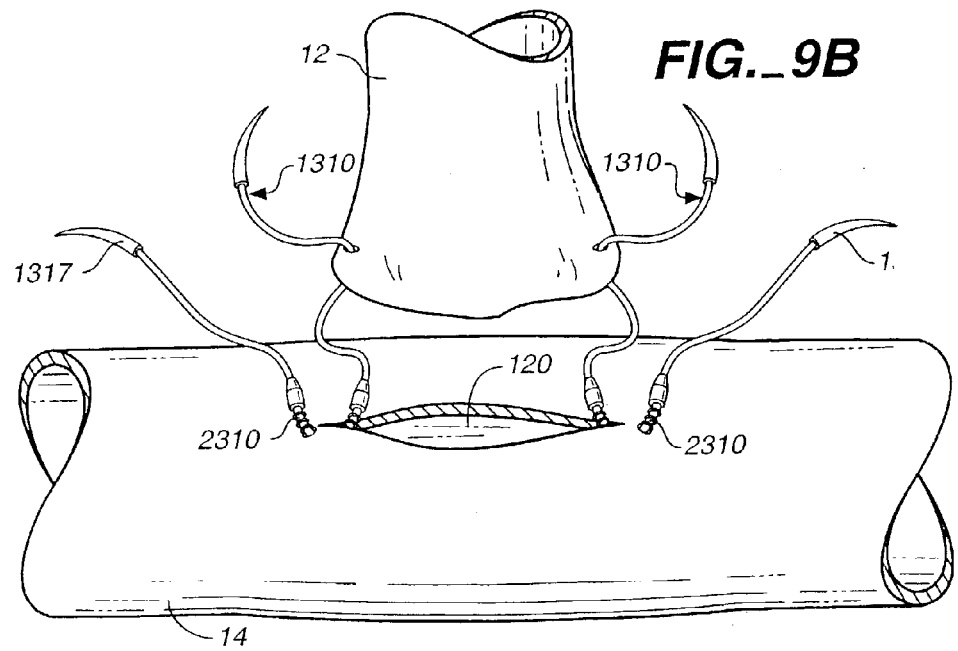
FIG._9B

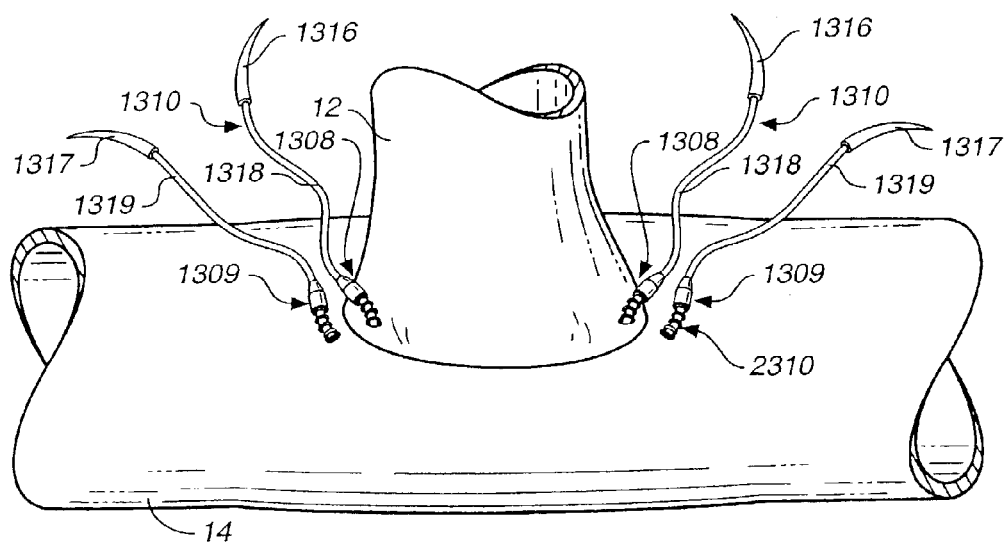
FIG._9C
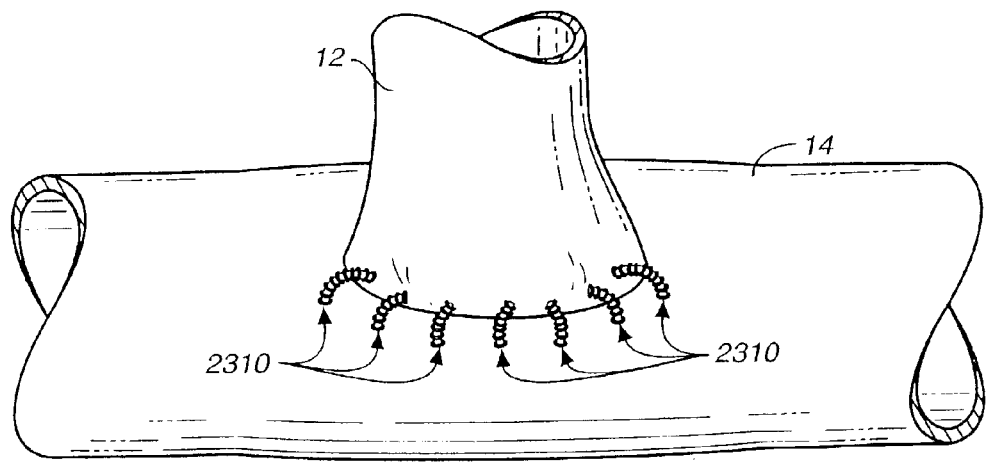
FIG._9D

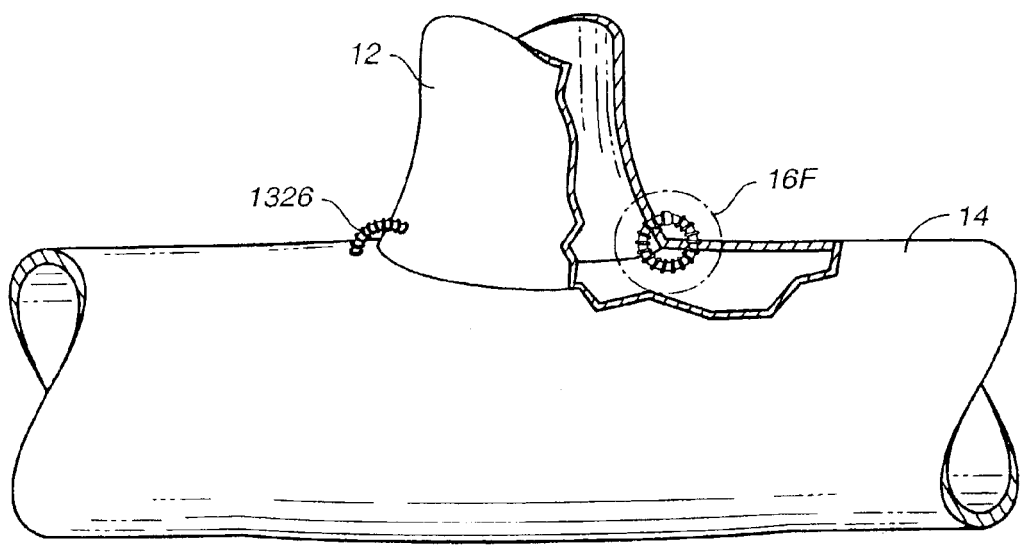
FIG._9E
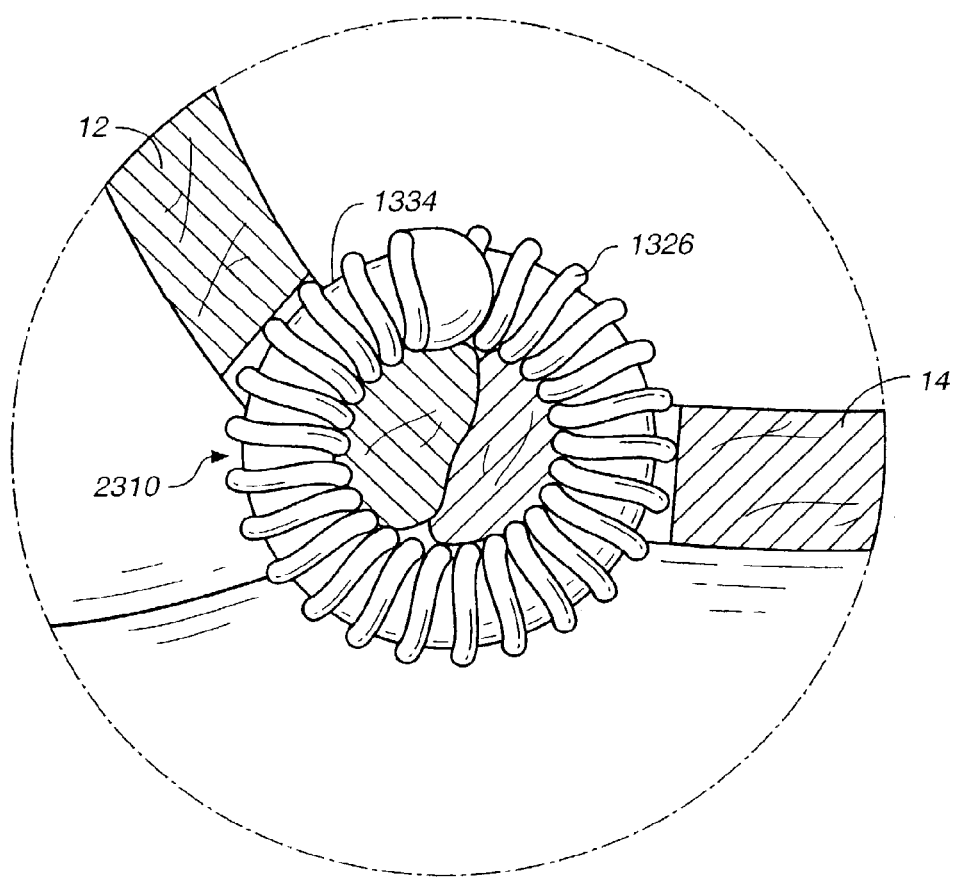
FIG._9F

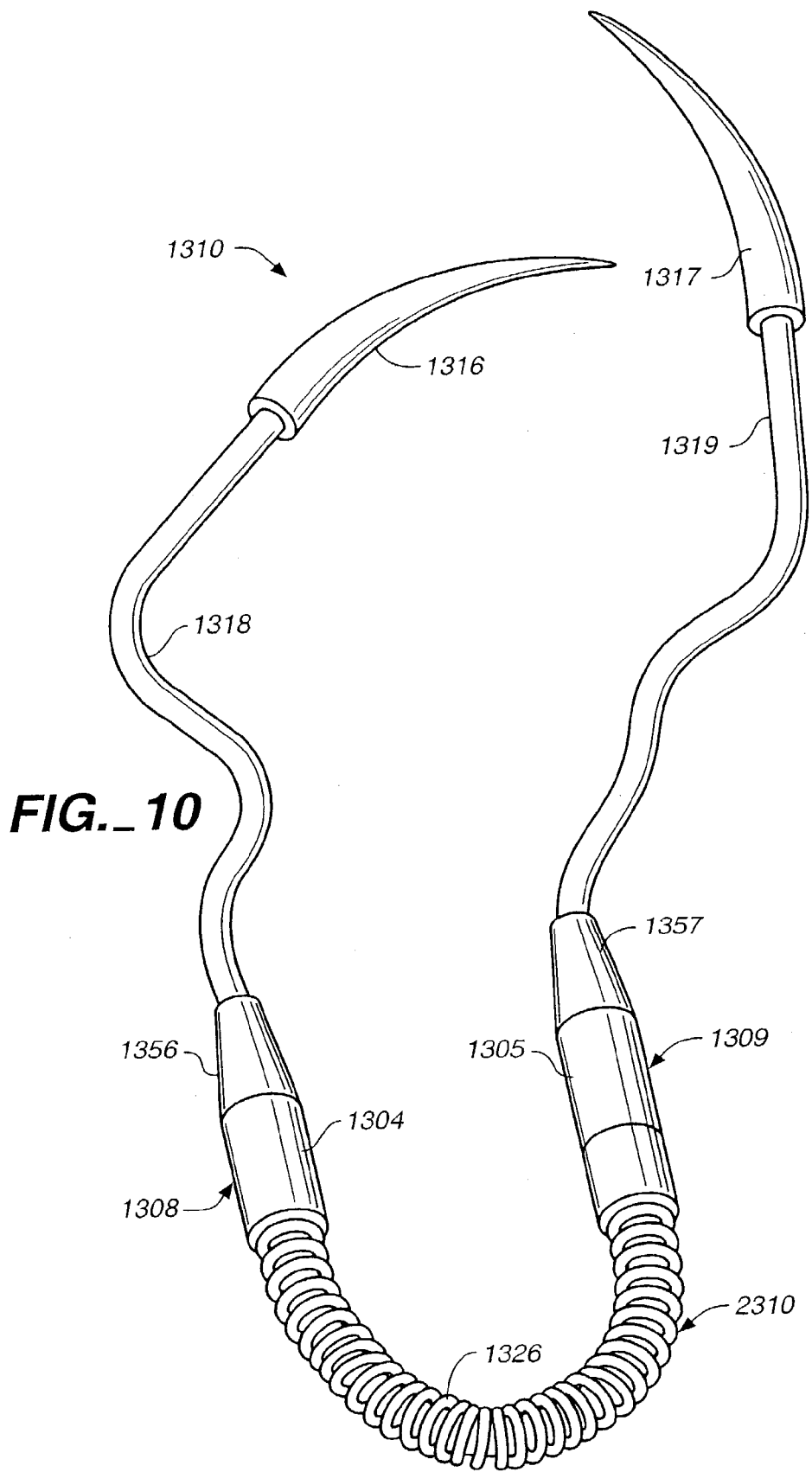
FIG._10

TISSUE CONNECTOR APPARATUS WITH CABLE RELEASE

CROSS REFERENCE TO RELATED APPLICATIONS

This application is a continuation of U.S. patent application Ser. No. 09/259,705 filed Mar. 1, 1999, the disclosure of which is incorporated by reference and which application issued as U.S. Pat. No. 6,514,265.

FIELD OF THE INVENTION

The present invention relates to instruments and methods for connecting body tissues, or body tissue to prostheses.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniature video camera, or optical telescope is inserted through one of these cannulas and a variety of surgical instruments and refractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connector assemblies.

SUMMARY OF THE INVENTION

The present invention involves improvements to devices for connecting tissues or tissue(s) and grafts, such as in a vascular anastomosis. The invention generally involves a surgical fastener which has an end portion that is releasably coupled to a plurality of strands that function as a release mechanism. One advantage of this release mechanism is that a needle or other piercing or penetrating member may be coupled to it to thereby releasably couple the needle, piercing member or penetrating member to the fastener.

Preferably, the surgical fastener comprises a shape memory material, most preferably nitinol. Preferably, the fastener comprises a wire. The wire may be a tubular wire. The wire preferably has a generally circular cross-section.

According to one aspect of the invention, a tissue connector assembly is provided with a clip movable between an open configuration and a closed configuration, and a mechanical restraining device coupled to the clip for restraining the clip in the open configuration. The mechanical restraining device includes a release in mechanism having a plurality of strands which may be releasably coupled to an enlarged portion of the clip.

The mechanical restraining device may include a coil surrounding at least a portion of the clip. The mechanical restraining device may further include a clip retainer fixed at an end portion of the clip opposite the enlarged end portion. Preferably, the clip retainer has a cross-sectional area greater than a cross-sectional area of the coil.

The coil includes a plurality of adjacent loops and is compressible with the plurality of adjacent loops being spaced closer to one another along one side of the coil than along an opposite side of the coil. Coupling of the release mechanism to the enlarged portion compresses the coil between the release mechanism and the retainer clip thereby biasing the clip in the open position.

The strands of the release mechanism may comprise substantially rigid wires. Alternatively, the strands may comprise substantially rigid cables. Each strand may include a notch for receiving part of the enlarged portion of the clip during releasable engagement.

The clip may have a generally U-shaped configuration when in the open configuration. A needle may be releasably attached to the clip to facilitate removal of the needle after insertion of the clip through the tissues/grafts. At least a portion of the mechanical restraining device may remain on the clip when the needle is released from the clip.

According to another aspect of the invention, the release mechanism of the tissue assembly may include a plurality of strands arranged in a circle and substantially parallel to one another to form a tube-like configuration, with proximal end portions of the strands being coupled to a needle. Alternatively, the proximal end portions may be coupled to a transition element which is connected to a needle by a flexible element, preferably a suture.

The distal end portions of the strands may include notches configured to receive and lock the enlarged portion of the clip within a chamber defined by the notches. A shrink wrap layer may be provided to surround at least the distal end portions of the strands, and is heat shrunk against the strands to compress the notches against the enlarged portion of the clip to more securely retain the enlarged portion. The shrink wrap layer may be a shrink tubing.

Compression of the plurality of strands in a location between the notches and the coupled proximal end portions, deforms the chamber to enable removal of the enlarged portion from the chamber. Removal of the enlarge portion from the chamber initiates closing of the clip. The clip is in a relaxed state when in the closed configuration. The clip may assume a spiral configuration in the closed configuration.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 1A is a front view of a tissue connector assembly of the present invention;

FIG. 1B is a partial enlarged view of the assembly of FIG. 1A taken along lines 1B—1B and 1B'—1B';

FIG. 1C is a partial sectional view of FIG. 1B taken along the longitudinal axis of the assembly;

FIG. 1D is a cross-sectional view of the assembly of FIG. 1B taken along line 1D—1D;

FIG. 1E is a view of the release mechanism of FIGS. 1A–1D, showing application of force to move the release mechanism to an open position;

FIG. 1F is a sectional view of the release mechanism being forced into an open position with the end of the clip being released therefrom;

FIG. 2A shows a graft vessel connected to a target vessel with tissue connector assemblies of FIG. 1;

FIG. 2B is a front view of the connected graft and target vessels of FIG. 2A, with portions broken away to show detail;

FIG. 2C is an enlarged view of the tissue connection shown in FIG. 2B;

FIG. 3A is an enlarged view of a fastener of the tissue connector assembly of FIG. 1 shown in a closed position;

FIG. 3B is a side view of the fastener of FIG. 3A;

FIG. 3C is an enlarged view of the fastener in an open position;

FIG. 3D is an enlarged view of an alternate configuration of the fastener shown in a closed position;

FIG. 3E is an enlarged view of an alternate configuration of the fastener shown in a closed position;

FIG. 3F is a side view of the fastener of FIG. 3E;

FIG. 3G is an enlarged view of an alternate configuration of the fastener shown in a closed position;

FIG. 4 is a perspective of a second embodiment of a tissue connector assembly of the present invention;

FIG. 5 shows two tissue connector assemblies of FIG. 4 in a first step for connecting a graft vessel to a target vessel;

FIG. 6 shows a second step for connecting the graft vessel to the target vessel;

FIG. 7 shows a third step for connecting the graft vessel to the target vessel;

FIG. 8 shows an alternate method for connecting the graft vessel to the target vessel with the tissue connector assemblies of FIG. 4;

FIGS. 9A–9D diagrammatically illustrate a method of aligning and connecting graft and target vessels with the tissue connector assemblies of FIGS. 1A and 10, where FIG. 9A shows two such tissue connector assemblies threaded through a graft and target vessel, FIG. 9B shows a further step in connecting the graft and target vessel with the tissue connector assembly fastener is positioned in the target vessel, FIG. 9C shows yet a further step where the graft has been brought into position over the opening formed in the target vessel and the tissue connector assembly fastener positioned through the walls of the graft and target vessel and FIG. 9D shows the fasteners released from the tissue connector assemblies of FIGS. 1A and 10 and securing the graft and target vessel together with additional laterally disposed fasteners;

FIG. 9E is a partial sectional view of the graft and target vessels with the tissue connector assembly fasteners of FIG. 10 in place prior to placement of additional lateral fasteners;

FIG. 9F is an enlarged view of the tissue connection within line 2F of FIG. 9E; and FIG. 10 is a perspective of a tissue connector assembly, constructed with a connector in accordance with the principles of the present invention, for use in a preferred method of anastomosis.

Corresponding reference characters indicate corresponding parts throughout the several views of the drawings.

DESCRIPTION OF THE INVENTION

The present invention generally involves devices for manipulating, aligning and/or connecting tissues, tissue and prosthesis, tissue and graft, or any combination thereof. As used herein, the term graft includes any of the following: homografts, xenografts, allografts, alloplastic materials, and combinations of the foregoing. Tissue connector assemblies are disclosed, which, for example, may be used in vascular surgery to replace or bypass a diseased, occluded, or injured artery by connecting a graft vessel to a coronary artery or vein in an anastomosis as shown in FIGS. 5–8 and 2A–2C. Assemblies constructed in accordance with the invention may be used in open surgical procedures or in minimally invasive or endoscopic procedures for attaching tissue located in the chest, abdominal cavity, or retroperitoneal space. It should be understood, however, that these examples are provided for illustration and are not intended to limit the scope of the invention.

Tissue connecting assemblies and methods are disclosed in copending U.S. patent application Ser. Nos. 09/089,884 and 09/090,305, both entitled Tissue Connector Apparatus and Methods and having a filing date of Jun. 3, 1998. The entirety of the disclosure of these applications is hereby incorporated herein.

Referring now to the drawings, and first to FIG. 1A, a tissue connector assembly constructed according to the principles of the present invention is shown and generally indicated with reference numeral 1. The tissue connector assembly 1 may be used to manipulate and align tissues, or tissue and graft with respect to each other and thereafter connect the tissues together (FIGS. 2A–2C). As used herein, the term graft includes any of the following: homografts, xenografts, allografts, alloplastic materials, and combinations of the foregoing. The tissue connector assembly 1 may be used in vascular surgery to replace or bypass a diseased, occluded, or injured artery by connecting a graft vessel 12 to a coronary artery 14 or vein in an anastomosis, for example. The tissue connector assembly 1 may be used in open surgical procedures or in minimally invasive or endoscopic procedures for attaching tissue located in the chest, abdominal cavity, or retroperitoneal space. These examples, however, are provided for illustration and are not meant to be limiting.

In the embodiment shown in FIG. 1A, the tissue connector assembly 1 generally comprises a penetrating member 102, and fastener or surgical clip 210. A restraining device, generally indicated at 108 and comprising a spring (or coil) 126 and a locking device or release mechanism generally indicated at 104, is connected to the fastener 210 for holding the fastener in a deformed configuration as further described below.

The penetrating member or needle 102 has a sharp pointed tip 30 at its distal end for penetrating tissue. The needle 102 may be bent as shown in FIG. 1A, for example. The distal end of the needle 102 is preferably rigid to facilitate penetration of tissue. The remaining length of the needle 102 may be rigid or flexible to facilitate movement of the needle through the tissue as further described below. The tip 30 of the needle 102 may be conical, tapered, or grounded to attain a three or four facet tip, for example. The needle 102 may be made from stainless steel or any other suitable material, such as a polymeric material. It is to be understood that the needle 102 may have a shape or radius of curvature other than the one shown, without departing from the scope of the invention.

The locking device or release mechanism 104 shown in FIGS. 1B–1F comprises a plurality of substantially rigid strands, preferably wires 106, arranged substantially parallel to one another and circularly about a longitudinal axis of the aligned strands, to form a tube-like configuration, as can be seen in the cross-section view of FIG. 1D and the perspective view in FIG. 1B. Alternatively, strands 106 may be cables or some other substantially rigid strand elements arranged in the same manner as the wires shown in FIG. 1D. Upon arrangement into the circular configuration, the proximal portions 106a of the strands are coupled to a needle 102 or transition sleeve 156 (FIG. 4) extending from the releasing mechanism to a flexible member to facilitate insertion of the releasing mechanism through tissue.

Preferably, a rod 162 extends from the needle or transition element to facilitate fixation of the strands. The coupling of the strands to the needle or transition element is preferably accomplished by gluing or soldering to the rod 162, although other equivalent or similar known joining techniques may be employed (e.g. welding, threadably attaching, etc). Similarly, the rod 162 is preferably glued, soldered or threaded into the needle or transition element.

The distal portions 106b of the strands contain notches 109 which are formed into the strands to a depth equal to approximately half the diameter of the strand 106. When the strands are arranged in the circular configuration described above, the notches 109 form a chamber 109' for receiving and holding a proximal end of the clip which is preferably an enlarged ball 136, but may be of an enlarged barrel shape, or other shape that may be easily grasped and easily released. The notches are preferably placed about 0.015" from the distal ends of the strands, but this distance, of course, can be modified, depending upon the amount of compression of the spring 126 that is desired when the ball 136 is inserted into and held by notches 109.

After placement of the ball 136 within the chamber formed by the notches 109, a shrink wrap layer, preferably a shrink tubing 110 is provided over at least the distal portions 106b of the wires or strands 106, and the tubing is heated to compress against the strands 106 and hold them in place, preferably symmetrically against the ball 136. Together, the tubing 110 and strands 106 effectively hold the ball 136 captive within the notches 109. Alternative plastic or elastic restraining members, such as various types of springs, for example, may be mounted around the distal portions of the wires or strands to aid in maintaining them in place, preferably symmetrically against the ball 136. Still further, strand members may be designed with an elastic spring force sufficient to maintain the notches in place with sufficient force to maintain the ball 136 captive in the notches 109 under the tensile forces normally experienced during a suturing procedure. Although a seven strand embodiment is illustrated in the accompanying figures, it should be understood that fewer or more than seven strands may be used. The number of strands may vary depending on, for example, the size of the clip as well as the cross-sectional size of the strands. Typically, the number of strands may range from two to ten. For use in coronary anastomosis, the number of strands preferably will range from five to seven, although other numbers may be used.

In assembling, enlarged portion 138 of wire 134 is placed in chamber 109'. Tubing 110 is wrapped around at least a portion of the strands (as shown in the drawings) and heated to maintain enlarged portion 138 captive within the cavity formed by the strands. Compression coil or spring 126 is slid over wire 134 and compressed against portions 106b such that the fastener is in its open configuration. Enlarged portion 136 may then be formed or attached to wire 134 to maintain the fastener in its open configuration.

The release mechanism 104 is movable between a locked position (FIGS. 1A–1D) and an unlocked position (FIGS. 1E–1F). In the locked position the ball 136 is held within the notches 109 and consequently, the coil 126 is held in its compressed position, thereby maintaining the clip 134 in its deformed or open position. In the unlocked position, the ball 136 is released from the notches, thereby allowing the coil 126 to expand, which causes the clip 134 to close. The closure conformation of the clip may be characterized by any of those described below and shown in FIGS. 2C–3G, for example.

Movement of the release mechanism to the open position is accomplished by applying a compressive force to the shrink tube 110 and bundle of strands 106, as shown in FIGS. 1E and 1F. Advantageously, the compressive force may be applied at any opposing locations around the circumference of the shrink tube as long as the implement applying the force is oriented at an angle to the strands, preferably substantially perpendicular thereto, to allow the implement to traverse the strands so as to deform the positions thereof when the force is applied. For example, the needle holder 144 could be rotated 90° (or virtually any other angle) with respect to the strands 106 as shown in the plane of the drawing, while retaining the capability of deforming the strands to an open position upon application of a compressive force. The compressive force is preferably applied using a standard needle holder 144 or forceps, although other tools could be used, preferably those with applicators narrower than the length of the shrink tube 110. As shown, the strands or wires 106 get distorted from their circular configuration under the compression. This change in shape stretches the shrink tube 110 from a circular configuration to a somewhat elliptical configuration, and removes some of the notches 109 from contact with the ball 136, as shown in FIG. 1E, thereby permitting removal of the ball 136 from within the chamber previously formed by notches 109 in the closed position.

As shown in FIG. 3A, one embodiment of a fastener 210 comprises a deformable wire 134 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire 134 is positioned within the tissue in its undeformed configuration, a residual stress is present to maintain the tissue tightly together (FIG. 2C). In order for the pseudoelastic wire 134 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8–10 degrees Celsius).

It is to be understood that the shape memory alloy may also be heat activated, or a combination of heat activation and pseudoelastic properties may be used, as is well known by those skilled in the art.

The cross-sectional diameter of the wire 134 and length of the wire will vary depending on the specific application. The diameter "d" of the wire 134 may be, for example, between 0.001 and 0.015 inch. For coronary bypass applications, the diameter is preferably between 0.001 and 0.008 inch with a diameter "D" of the loop being between 0.0125 and 0.0875 inch (FIG. 3A). The diameter "D" of the loop of the fastener 210 in its closed position is preferably sized to prevent movement between adjacent tissues. As shown in FIGS. 3A and 3B, the wire 134 may have a circular cross-sectional shape, and a generally ring or loop-shaped configuration when in an closed position. It is to be understood that the wire may have other cross-sectional shapes such as rectangular, or may be formed from multiple strands without departing from the scope of the invention.

The retainer 138 has a cross-sectional area greater than the cross-sectional area of the coil 126 to prevent the wire and coil from passing through the tissue (FIG. 3C). The retainer 138 may be attached to the end of the wire 134 by welding, gluing or other suitable attachment means or may be formed integrally with the wire by deforming the end of the wire, but it is preferably crimped thereon, as described above. The retainer 138 may also be made to have a cross sectional area substantially equal to or less than the cross-sectional area of the coil 126, to facilitate pulling the fastener completely through the tissue, if, for example, the entire fastener needs to be removed from the vessel during the insertion procedure. The distal end of the wire 134 includes an enlarged portion 138 for engagement with the restraining device 108 as further described below (FIG. 4A). The enlarged portion 138 may be formed by deforming the end of the wire 134 by swaging or arc welding, or attaching by welding, swaging, or other suitable means to form an enlarged portion at the end of the wire.

The wire 134 has an undeformed or closed position (state or configuration) (FIG. 3A) for keeping or connecting tissue together, and a deformed or open position (state or configuration) (FIG. 3C) for insertion of the wire into tissue. The wire 134 is preferably not deformed past its yield point in its open position. Accordingly, it may have a U-shaped configuration in its open position to facilitate insertion of the wire 134 through the tissue. It is to be understood that a U-shaped configuration may be alternatively substituted by an equivalent structure such as C-shaped, V-shaped, J-shaped, and other similarly shaped configurations. The wire 134 is moved from its closed position to its open position by the restraining device 108, as further described below. When in its closed position, the wire 134 forms a loop with the ends of the wire in a generally side-by-side or overlapping orientation (FIG. 3B).

The wire 134 may be formed in the above described shape by first wrapping the wire onto a mandrel and heat treating the wire at approximately 400–500 degrees Celsius for approximately 5 to 30 minutes. The wire 134 is then air quenched at room temperature. The mandrel may have a constant diameter or may be conical in shape.

An alternate configuration of the surgical clip 210 in its closed position is shown in FIG. 3D, and generally indicated at 40. The fastener 40 forms a spiral configuration in its closed position for trapping tissue within a loop formed by the spiral. In its open position, the fastener 40 is configured to form less than a full 360 degree turn.

Another alternate configuration of the surgical clip 210 is shown in FIGS. 3E and 3F in its closed position, and is generally indicated at 41. The fastener 41 is formed in a spiral about a central longitudinal axis A. As shown in FIG. 3F, the fastener 41 has a generally conical shape along the longitudinal axis A, with a decreasing diameter as the radius of curvature of the fastener 41 decreases. The fastener 41 has an inner end portion 45 and an outer end portion 47, with the enlarged portion 136 of the wire being disposed at the outer end portion for engagement with the release mechanism 104 (FIG. 3E).

A modification of the fastener is shown in FIG. 3G, and generally indicated at 43. The fastener 43 is the same as the fastener 41 described above, except that the enlarged portion 136, which is adapted for engaging a release mechanism, is positioned at the inner end portion 45 of the fastener. Placement of the release mechanism 104 at the inner end portion 45 of the fastener 43 increases the compression force of the wire in its undeformed position on the tissue and decreases the surface area of the fastener exposed to blood flow.

It is to be understood that the fastener 210, 40, 41, 43 may have undeformed or deformed configurations different than those shown herein without departing from the scope of the invention. In addition, a locking clip (not shown) may also be attached to connect the ends of the fastener 210, 40, 41, 43 when the fastener is in its closed position to prevent possible opening of the fastener over time. The locking clip may also be integrally formed with one end of the fastener.

As shown in FIG. 3C, the wire 134 is surrounded by the spring or coil 126 which, along with the locking device 104 and clip retainer 138, restrains the wire in its deformed configuration. The coil 126 comprises a helical wire forming a plurality of loops which define a longitudinal opening 44 for receiving the shape memory alloy wire 134. The coil 126 may be formed from a platinum alloy wire having a cross-sectional diameter of approximately 0.0005–0.005 inch, for example. The wire may have other cross-sectional shapes and be formed of different materials. The coil 126 is preferably sized so that when in its free (uncompressed state) it extends the length of the wire 134 with one end adjacent the clip retainer 138 at the distal end of the wire and the other end adjacent the enlarged portion 136 at the proximal end of the wire (FIG. 3B). It is to be understood that the spring 126 may not extend the full length of the wire. For example, a flange or similar device may be provided on an intermediate portion of the wire 134 to limit movement of the coil along the length of the wire.

When the coil 126 is in its free state (with the wire 134 in its undeformed configuration), loops of the coil are generally spaced from one another and do not exert any significant force on the wire 134 (FIG. 3A). When the coil 126 is compressed (with the wire 134 in its deformed configuration), loops of the coil on the inner portion 46 of the coil are squeezed together with a tight pitch so that the loops are near or contiguous with one another while loops on the outer portion 48 of the coil are spaced from one another (FIG. 3C). This is due to the compressed inner arc length of the coil 126 and the expanded outer arc length of the coil. The compression of the loops on the inner portion 46 of the coil 126 exerts a force on the inner side of the wire 134 which forces the wire to spread open (i.e., tends to straighten the wire from its closed configuration to its open configuration). The end of the coil 126 adjacent the clip retainer 138 is held in a fixed position relative to the wire 134. The opposite end of the coil 126 is free to move along the wire 134 and is held in place when the coil is in its compressed position by the locking device 104 (FIG. 4A). It should be understood, however, that a coil (not shown) having sufficient stiffness, for example, may be used where adjacent loops do not contact one another when the coil is compressed to force the wire 134 into an open position.

Another embodiment of the tissue connector assembly is shown in FIG. 4 and generally indicated with reference numeral 310. The tissue connector assembly 310 is similar to the tissue connector assembly 1 of the first embodiment, except that a flexible member 318 is inserted between a restraining device 108 and needle 316. FIG. 4 shows the tissue connector assembly 310 with a fastener 210 in an open (deformed) position. The fastener 210 may be the same as any of the fasteners 210, 40, 41, 43 described above and shown in FIGS. 3A–3G for the tissue connector assembly 1 of the first embodiment, for example. The fastener 210 includes the restraining device 108 comprising a coil 126 and a release mechanism 104. The release mechanism 104 is the same as the release mechanism or locking device 104 described above, but is instead connected to a transition sleeve 156.

The flexible member 318 is attached to the distal end of the locking device 104 by the tapered portion or transition sleeve 156 extending from the locking device 104 to the flexible member 318 to facilitate insertion of the locking device through tissue. The tapered sleeve 156 is preferably sufficiently curved to facilitate movement of the tissue connector assembly 310 through connecting tissue in an anastomosis, for example. The sleeve 156 may be formed from a metal alloy such as stainless steel or a suitable polymeric material. The needle 316 may be swaged into the sleeve 156, or a heat shrink plastic covering may hold the needle in place. The locking device 104 may also be curved.

The flexible member 318 may be in the form of a suture formed from conventional filament material, metal alloy such as nitinol, polymeric material, or any other suitable material. The material may be non-stretchable or stretchable, solid or hollow, and have various cross-sectional diameters. The suture may have a cross-sectional diameter of 0.003 inch, for example. The diameter and length of the suture will vary depending on the specific application. The suture may be attached to the needle 316 by crimping or swaging the needle onto the suture, gluing the suture to the needle, or any other suitable attachment method. The flexible member 318 may have cross-sectional shapes other than the one shown herein.

The needle 316 may be integrally formed with the flexible member 318. The diameter of at least a portion of the needle 316 is preferably greater than the diameter of the flexible member 318 so that the flexible member can easily be pulled through an opening formed in the tissue by the needle.

As noted above, the tissue connector assemblies 1, 310 of this invention have many uses They may be especially useful in minimally invasive surgical procedures including creating an anastomosis between a vascular graft 12 and an artery 14 (FIGS. 2A–2C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastro-epiploic artery in the abdomen, radial artery, and other arteries harvested from the patient's body as well as synthetic graft materials, such as DACRON® or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

FIGS. 2A–2C and 5–7 show an exemplary use of the tissue connector assemblies 1, 310 for connecting a graft vessel 12 to an artery 14 (target vessel). In this example, two tissue connector assemblies 310 (FIG. 5) are used to make connections at generally opposite sides of the graft vessel and a plurality of tissue connector assemblies 1 (FIG. 1A) are used to make connections between those made with tissue connector assemblies 310. The procedure may be accomplished with a beating heart procedure with the use of a heart stabilizer to keep the heart stable, for example. The procedure may also be performed endoscopically.

The patient is first prepped for standard cardiac surgery. After exposure and control of artery 14, occlusion and reperfusion may be performed as required, an arteriotomy is performed on artery 14 to provide an opening 121 for receiving a graft vessel. Referring to FIGS. 5–7, after the arteriotomy of the snared graft vessel 12 has been made to the appropriate length, as would be apparent to one of ordinary skill in the art, a tissue connector assembly 310 is attached to the free end of the graft vessel along an edge margin of the vessel. In order to attach the connector assembly 310, the surgeon grasps the needle 316 with a needle holder (e.g., surgical pliers, forceps, or any other suitable instrument) and inserts the needle 316 into an end margin of the graft vessel 12 in a direction from the exterior of the vessel to the interior of the vessel. The surgeon then releases the needle 316 and grasps a forward end of the needle which is now located inside the graft vessel 12 and pulls the needle and a portion of the suture 318 through the vessel. The needle 316 is passed through an opening 121 formed in the sidewall of the artery 14 and inserted into the tissue of the artery in a direction from the interior of the artery to the exterior of the artery. The surgeon then grasps the needle 316 located outside the artery 14 and pulls the needle and a portion of the suture 318 through the arterial wall. A second tissue connector assembly 310 may be inserted at a location generally 180 degrees from the location of the first tissue connector in a conventional "heel and toe" arrangement. Alternatively, a number of tissue connectors 310 may be inserted generally around the location of the heel. The graft vessel 12 may then be pulled towards the artery 14 to determine whether the opening 121 formed in the sidewall of the artery is large enough before completing the anastomosis.

Once the tissue connector assemblies 310 are inserted, the graft vessel 12 is positioned above the opening 121 in the sidewall of the artery 14 (FIG. 5). The fasteners 210 and needles 316 are pulled generally away from the artery 14 to reduce the length of the suture 318 between the vessel 12 and artery and "parachute" the vessel onto the artery (FIG. 6). The needles 316 are then pulled away from the artery 14 until the fastener 210 is positioned within the graft vessel 12 and artery with one end of each fastener extending from the vessel and the opposite end of each fastener extending from the artery (FIG. 7). The edges of the graft vessel 12 and artery 14 are positioned adjacent one another to form a continuous interior and exterior surface along the mating portions of the vessel and artery. As shown in FIG. 2C, the tissue is compressed within the fastener 210.

A surgical instrument (e.g., needle holder) is used to radially squeeze each release mechanism 104 to release it from the fastener 210, as described above with reference to FIGS. 1E–1F. Upon removal of the locking device 104, the coil 126 moves to its free uncompressed state which allows the wire 134 to return to its original undeformed closed position (FIG. 2A). As the wires 134 move to their closed position the adjacent tissues of the graft vessel 12 and artery 14 which were previously pulled together during the parachuting of the graft vessel onto the artery, are squeezed together to securely engage the graft vessel and artery (FIGS. 2B and 2C).

The tissue connector assemblies 1 are subsequently inserted at circumferentially spaced locations around the periphery of the graft vessel 12 to sealingly fasten the graft vessel to the artery 14. The needle 102 of the fastener 1 is inserted into the graft vessel 12 from the exterior surface of the graft vessel and pushed through the graft vessel and artery 14 tissue. The needle holder is then used to pull the needle 102 through the arterial wall. An instrument (same needle holder or other suitable instrument) is used to apply a squeezing force to the release mechanism 104 to release the wire 134 and coil 126 from the needle 102. This allows the coil 126 to move to its uncompressed configuration and the wire 134 to move to its closed position. It should be noted that the tissue connector assemblies 310 may remain in their open position while the tissue connector assemblies 1 are inserted into the tissue and moved to their closed position. The release mechanisms 104 of the tissue connector assemblies 310 may subsequently be removed from the fasteners 210 to allow the fasteners to move to their closed position. The number and combination of tissue connectors assemblies 1, 310 required to sealingly secure the connecting tissues together may vary. For example, only tissue connector assemblies 1 may be used to complete the entire anastomosis, or only tissue connector assemblies 310 may be used to connect tissues.

It should be noted that as the release mechanism 104 is squeezed two steps are accomplished. The fastener 210 is released from the release mechanism 104, thus allowing the coil 126 to uncompress and the wire 134 to move to its closed configuration, and the needle 102 is released from the fastener 210. Thus, in the embodiment shown, the release mechanism 104 provides for simultaneous actuating closure of the fastener 210 and release of the needle 102 from the fastener.

The graft vessel 12 may also be parachuted onto the artery 14 in the method shown in FIG. 8. The needles 316 are inserted into the graft vessel 12 and artery 14 as described above and the sutures 318 are pulled through the vessel so that the fasteners 120 are positioned within the vessel. The needles 316 are then pulled away from the artery 14 to "parachute" the graft vessel 12 onto the artery.

FIGS. 9A–9D diagrammatically illustrate a preferred method of aligning and connecting graft and target vessels, such as connecting a graft vessel 12 to an artery 14 (target vessel) using tissue connector assemblies 1310 as shown in FIG. 10. The tissue connectors 1310 are a modification of the embodiments described above so as to include two tissue piercing or penetrating members 1316 and 1317, flexible members 1318 and 1319, and fastener or surgical clip 2310. Note also that the method described with regard to FIGS. 9A–9D can also be practiced using tissue connectors having two piercing members and only one flexible member. Although these devices are not specifically shown herein, a complete description of the same, as well as the connectors having dual piercing members and flexible members, and the preferred method, can be found in copending application Ser. No. 09/260,623, titled "Tissue Connector Apparatus and Methods", filed concurrently herewith. Copending application Ser. No. 09/260,623, is hereby expressly incorporated by reference in its entirety.

Connector 1310 includes restraining devices, generally indicated at 1308 and 1309 which are similar or identical to restraining device 108, and comprising a spring (or coil) 1326 and a locking device or release mechanism generally indicated at 1304 and 1305, which are similar to or the same as release mechanism 104, for holding the fastener 2310 in a deformed or open configuration as described above with regard to fastener 210. Although a particular fastener and accompanying restraining device is shown in FIG. 10, it should be understood that any suitable fastener can be used for the method to be described, including but not limited to the alternate fastener configurations described in the copending application Ser. No. 09/260,623 and cited above. For example, the fastener or surgical clip may be a plastically deformable clip or may comprise two or more parts, at least one of which is movable relative to the other part, such as with a hinged clip. Further, other piercing member release mechanisms can be used with or without restraining devices depending on the fastener construction.

Each of penetrating or piercing members 1316 and 1317 may be in the form of a needle having a sharp pointed tip at its distal end for penetrating tissue. Needles 1316 and 1317 may be bent as shown in FIG. 10, for example. The diameter of at least a portion of each of needles 1316 and 1317 is preferably greater than the diameter of the respective flexible members (1318 and 1319), coupled thereto so that the flexible members can easily be pulled through an opening formed in the tissue (or other material) by the needle. The distal ends of the needles 1316 and 1317 are preferably rigid to facilitate penetration of tissue. The remaining length of the needles 1316 and 1317 may be rigid or flexible to facilitate movement of the needle through the tissue as further described below. The needle tips may have various configurations and may, for example, be conical, tapered, or grounded to attain a three or four facet tip. Needles 1316 and 1317 may be made from stainless steel or any other suitable material, such as a polymeric material. It is to be understood that the needles 1316 and 1317 may have a shape or radius of curvature other than the one shown, without departing from the scope of the invention. Needles 1316 and 1317 may also be integrally formed with the flexible member 1318 (e.g., both needle and flexible member formed of the same material.)

The flexible members 1318 and 1319 may be in the form of a suture formed from conventional filament material, metal alloy such as nitinol, polymeric material, or any other suitable material. The material may be non-stretchable or stretchable, solid or hollow, and have various cross-sectional diameters. The flexible members or sutures may have a cross-sectional diameter of 0.003 inch, for example. The diameter and length of the suture will vary depending on the specific application. The sutures may be attached to the needles 1316 and 1317, respectively, by crimping or swaging the needle onto the suture, gluing the suture to the needle, or any other suitable attachment method. Flexible members 1318 and 1319 may have cross-sectional shapes other than the one shown herein.

Transition sleeves 1356 and 1357, which are similar to or the same as transition sleeve 156 described above, extend from respective releasing mechanisms 1308 and 1309 to flexible members 1318 and 1319 to facilitate insertion of the releasing mechanism through tissue.

Returning to the method in FIGS. 9A–9D, two tissue connector assemblies 1310 are used to make connections at generally opposite sides of the graft vessel and tissue connector assemblies 1 are used to make connections between those made with assemblies 1310. The procedure may be accomplished with a beating heart procedure with the use of a heart stabilizer to keep the heart stable, for example. The procedure may also be performed endoscopically.

The patient is first prepped for standard cardiac surgery. After exposure and control of artery 14, occlusion and reperfusion may be performed as required. An arteriotomy is performed on artery 14, as described above with regard to opening 121, to provide an opening 120 for receiving a graft vessel. After the arteriotomy of the snared graft vessel 12 has been made to the appropriate length, a tissue connector assembly 1310 is attached to the free end of the graft vessel along an edge margin of the vessel, in the manner described previously. Needle 1317 is passed through the opening 120 formed in the sidewall of the artery 14 and inserted into the tissue of the artery in a direction from the interior of the artery to the exterior of the artery. The surgeon then grasps needle 1317 located outside the artery 14 and pulls the needle and a portion of suture 1319 through the arterial wall. A second tissue connector assembly 1310 may be inserted as described above at a location generally 180 degrees from the location of the first tissue connector in a conventional "heel and toe" arrangement.

Once the tissue connector assemblies 1310 are inserted, graft vessel 12 is positioned above and aligned with opening 120 in the sidewall of the artery 14 (FIG. 9A). A section of each assembly is located between graft vessel 12 and artery 14. The needles 1316 and 1317 are pulled to perform the previously described "parachuting" of the vessel onto the artery (FIG. 9B). The needles 1317 are then pulled away from the artery 14 until each fastener 2310 is positioned within the target vessel 14 as shown in FIG. 9B. Needles 1316 are then pulled away from graft 12 until the fasteners are positioned with one end of each fastener 2310 extending from the vessel and the opposite end of each fastener extending from the artery (FIG. 9C). The edges of the graft vessel 12 and artery 14 are positioned adjacent one another to form a continuous interior and exterior surface along the mating portions of the vessel and artery. As shown in FIG. 9F, the tissue is compressed within the fastener 2310.

A surgical instrument (e.g., needle holder) is used to radially squeeze each release mechanism 1304, 1305 to release the release mechanisms from the fastener 2310. Upon removal of each release mechanism, each coil 1326 moves to its free uncompressed state which allows fastener wire 1334 to return to its original undeformed closed position (FIG. 9D). As the wires 1334 move to their closed position the adjacent tissues of the graft vessel 12 and artery 14 which were previously pulled together during the parachuting of the graft vessel onto the artery, are squeezed together to securely engage the graft vessel and artery (FIGS. 9E and 9F). It should be noted that as each locking device 1304, 1305 is squeezed at least two steps are accomplished. The fastener 2310 is released from locking device, thus allowing coil 1326 to uncompress and the wire 1334 to move to its closed configuration, and the needle 1316, 1317 is released from the fastener. Further, radially compression of release mechanisms 104, 105 releases needles 1316, 1317 and sutures 1318, 1319 from the fasteners. However, a synchronous release system described in the copending application Ser. No. 09/260,623 may be used, wherein radial compression of a locking device will effect essentially simultaneous closure actuation of a respective fastener and release of needles 1316 and 1317 and sutures 1318 and 1319.

The tissue connector assemblies 1 are subsequently inserted at circumferentially spaced locations around the periphery of the graft vessel to sealingly fasten graft vessel 12 to artery 14. Needle 102 of fastener 1 is inserted into graft vessel 12 from the exterior surface of the graft vessel and pushed through the graft vessel and artery 14 tissue. The needle holder is then used to pull the needle 102 through the arterial wall. An instrument (same needle holder or other suitable instrument) is used to apply a squeezing force to the locking device 104 to release fastener 210 from needle 102. This allows coil 126 to move to its uncompressed configuration and the wire to move to its closed position. It should be noted that the tissue connector assemblies 1310 may remain with their fasteners in their open position while tissue connector assemblies 1 are inserted into the tissue and moved to their closed position. The locking devices 104, 105 of the tissue connector assemblies 1310 may subsequently be removed from the fasteners 2310 to allow the fasteners to move to their closed position. The number and combination of tissue connectors assemblies 1310, 1 required to sealingly secure the connecting tissues together may vary. For example, only tissue connector assemblies 1310 may be used to complete the entire anastomosis.

As an alternative to inserting tissue connector assemblies 1310 at "heel and toe" locations described above, a number of tissue connectors 1310 may be inserted generally around the location of the heel. The graft vessel may then be pulled towards the artery to determine whether the opening formed in the sidewall of the artery is large enough before completing the anastoinosis.

Although the coil 126, 1326 is shown as remaining on the wire in each of the above-described procedures, it is to be understood that the coil 126, 1326 may also be removed from the wire 134, 1334, leaving only the wire in the connected tissue.

Although the suturing procedures have been described for an end-to-side anastomosis, it should be appreciated that the procedures are also applicable to an end-to-end and side-to-side anastomosis, connecting various tissue structures including single and multiple tissue structures, and puncture sites, and connecting tissue to a prosthetic graft or valve, for example.

It will be observed from the foregoing that the tissue connector assemblies of the present invention have numerous advantages. Importantly, the assemblies are easier and faster to apply than conventional sutures which require tying multiple knots. The assemblies may be used in minimally invasive procedures including endoscopic procedures, and may be inserted single handedly.

All references cited above are incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tissue connector assembly comprising a clip movable between an open configuration and a closed configuration, said clip having an enlarged end portion, and a release mechanism comprising a plurality of strands releasably coupled to said enlarged portion, and retaining said clip in said open configuration wherein said strands each comprise a notch for receiving part of said enlarged portion.

2. The tissue connector assembly of claim 1, wherein distal end portions of said strands comprise notches configured to receive and lock said enlarged portion within a chamber defined by said notches.

3. The tissue connector assembly of claim 2, further comprising a shrink wrap layer surrounding at least said distal end portions of said strands, said shrink wrap layer adapted to be heat shrunk against said strands, thereby compressing said notches against said enlarged portion.

4. The tissue connector assembly of claim 3, wherein said shrink wrap layer comprises a shrink tubing.

5. The tissue connector assembly of claim 2, wherein distal end portions of said strands comprise notches configured to receive and lock said enlarged portion within a chamber defined by said notches; and wherein compression of said plurality of strands in a location between said notches and said coupled proximal end portions, deforms said chamber to enable removal of said enlarged portion from said chamber.

6. A tissue connector assembly comprising a clip movable between an open configuration and a closed configuration, said clip having an enlarged end portion, a release mechanism comprising a plurality of strands releasably coupled to said enlarged portion, and retaining said clip in a said open configuration and a needle connected to said release mechanism and thereby releasably attached to said clip.

7. The tissue connector assembly of claim 6, wherein said strands comprise substantially rigid wires.

8. The tissue connector assembly of claim 6, wherein said strands comprise substantially rigid cables.

9. The tissue connector assembly of claim 6, wherein said clip has a generally U-shaped configuration when in said open configuration.

10. The tissue connector assembly of claim 6, wherein said plurality of strands are arranged in a circle and substantially parallel to one another to form a tube-like configuration, with proximal end portions of said strands being coupled to said needle.

11. The tissue connector assembly of claim 6, wherein compression of said plurality of strands releases said release mechanism from said enlarged portion.

12. A tissue connector assembly comprising a clip movable between an open configuration and a closed configuration, said clip having an enlarged end portion, a release mechanism comprising a plurality of strands releasably coupled to said enlarged portion, and a coil surrounding at least a portion of said clip and biasing said clip toward the open configuration.

13. The tissue connector assembly of claim 12, further comprising a clip retainer fixed at an end portion of said clip opposite said enlarged end portion.

14. The tissue connector assembly of claim 13, wherein said coil comprises a plurality of adjacent loops, said coil being compressible with said plurality of adjacent loops being spaced closer to one another along one side of said coil than along an opposite side of said coil.

15. The tissue connector assembly of claim 14, wherein coupling of said release mechanism to said enlarged portion compresses said coil between said release mechanism and said retainer clip thereby biasing said clip in said open position.

16. The tissue connector assembly of claim 13, wherein said clip retainer has a cross-sectional area greater than a cross-sectional area of said coil.

17. The tissue connector assembly of claim 12, wherein said clip comprises a wire.

18. The tissue connector assembly of claim 17, wherein said wire is tubular.

19. The tissue connector assembly of claim 17, wherein said wire has a generally circular cross-section.

20. The tissue connector assembly of claim 17, wherein said wire comprises shape memory material.

21. A tissue connector assembly comprising a clip movable between an open configuration and a closed configuration, said clip having an enlarged end portion, and a release mechanism comprising a plurality of strands releasably coupled to said enlarged portion, and retaining said clip in said open configuration wherein said clip assumes a spiral configuration in said closed configuration.

22. The tissue connector assembly of claim 21, wherein said clip is in a relaxed state when in said closed configuration.

23. The tissue connector assembly of claim 21, wherein said plurality of strands comprises two to ten strands.

24. A tissue connector assembly comprising a clip adapted to assume an open configuration and a closed configuration, a coil coupled to said clip, and a release mechanism comprising a plurality of strands releasably coupled to said clip, wherein said coil biases said clip in said open configuration when said release mechanism is coupled to said clip.

25. The tissue connector assembly of claim 24, further comprising a needle coupled to said release mechanism.

26. The tissue connector assembly of claim 25, wherein said plurality of strands are arranged in a circle and substantially parallel to one another to form a tube-like configuration, with proximal end portions of said strands being coupled to said needle.

27. The tissue connector assembly of claim 26, wherein distal end portions of said strands comprise notches configured to receive and lock an enlarged portion of said clip within a chamber defined by said notches.

28. The tissue connector assembly of claim 27, further comprising a shrink wrap layer surrounding at least said distal end portions of said strands, said shrink wrap layer adapted to be heat shrunk against said strands, thereby compressing said notches against said enlarged portion.

29. The tissue connector assembly of claim 28, wherein compression of said plurality of strands in a location between said notches and said coupled proximal end portions, deforms said chamber to enable removal of said enlarged portion from said chamber.

30. The tissue connector assembly of claim 28, wherein said shrink wrap layer comprises a shrink tubing.

31. The tissue connector assembly of claim 25 wherein said needle is releasable from said clip simultaneously with said release mechanism.

32. The tissue connector of claim 31, wherein said clip assumes said closed position upon release from said release mechanism.

33. The tissue connector assembly of claim 24, further comprising a needle and a flexible member, said flexible member coupling said needle to said release mechanism.

34. The tissue connector assembly of claim 33, further comprising a transition sleeve connecting said release mechanism to said flexible member.

35. The tissue connector assembly of claim 33, wherein said flexible member compnses a suture.

36. The tissue connector assembly of claim 24 wherein compression of said plurality of strands releases said release mechanism from said clip.

37. The tissue connector assembly of claim 24, wherein said plurality of strands comprises two to ten strands.

* * * * *